US012637401B2

(12) United States Patent
Gordon et al.

(10) Patent No.: US 12,637,401 B2
(45) Date of Patent: May 26, 2026

(54) SEPARATION PROCESS FOR THE PRODUCTION OF C5 OR C6 ALKANEDIOL

(71) Applicant: JOHNSON MATTHEY DAVY TECHNOLOGIES LIMITED, London (GB)

(72) Inventors: Paul Gordon, Stockton-on-Tees Cleveland (GB); Maria del Amo Lopez, London (GB); Graham Reed, London (GB); Michael Winter, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 283 days.

(21) Appl. No.: 18/559,223

(22) PCT Filed: Jul. 4, 2022

(86) PCT No.: PCT/GB2022/051712
§ 371 (c)(1),
(2) Date: Nov. 6, 2023

(87) PCT Pub. No.: WO2023/281247
PCT Pub. Date: Jan. 12, 2023

(65) Prior Publication Data

US 2024/0270667 A1 Aug. 15, 2024

(30) Foreign Application Priority Data

Jul. 5, 2021 (GB) ..................................... 2109710

(51) Int. Cl.
*C07C 29/80* (2006.01)
*B01D 3/14* (2006.01)
(Continued)

(52) U.S. Cl.
CPC .............. *C07C 29/80* (2013.01); *B01D 3/141* (2013.01); *C07C 29/149* (2013.01); *C07C 31/20* (2013.01)

(58) Field of Classification Search
CPC ........ C07C 29/80; C07C 29/149; B01D 3/141
See application file for complete search history.

(56) References Cited

U.S. PATENT DOCUMENTS 5,981,769 A 11/1999 Baur et al.
6,008,418 A 12/1999 Baur et al.
(Continued)

FOREIGN PATENT DOCUMENTS

CN 102666456 B 5/2015
EP 2614056 B1 7/2013
EP 2 351 726 B1 2/2015

*Primary Examiner* — Renee Robinson
(74) *Attorney, Agent, or Firm* — BakerHostetler

(57) ABSTRACT

A process for separating a Cs or C6 alkanediol from a crude product stream comprising the Cs or C6 alkanediol, light contaminants and heavy contaminants comprising one or more of: a C 10 or C 12 linear ester, or a C 10 or C 12 cyclic acetal or ketal is disclosed. The process comprises feeding the crude product stream to a separation system comprising a first distillation zone, to which the crude product stream is fed and from which the heavy contaminants are removed in a heavies stream taken as a bottom stream, and a second distillation zone, in which the Cs or C6 alkanediol is separated from a reaction product, comprising one or more of: a Cs or C6 cyclic ester, or a Cs or C6 aldehyde, formed in the first distillation zone and from which the Cs or C6 alkanediol is withdrawn in a refined product stream.

17 Claims, 6 Drawing Sheets

(51) Int. Cl.
*C07C 29/149* (2006.01)
*C07C 31/20* (2006.01)

(56) References Cited

U.S. PATENT DOCUMENTS

| | | | |
|---|---|---|---|
| 6,288,286 | B1 | 9/2001 | Stein et al. |
| 6,727,395 | B1 | 4/2004 | Stein et al. |
| 7,064,239 | B2 | 6/2006 | Fischer et al. |
| 7,329,330 | B2 | 2/2008 | Gall et al. |
| 8,513,472 | B2 | 8/2013 | Li et al. |
| 2004/0040829 | A1 | 3/2004 | Gall et al. |
| 2011/0124925 | A1 | 5/2011 | Pinkos |

SEPARATION PROCESS FOR THE PRODUCTION OF C5 OR C6 ALKANEDIOL

FIELD OF THE INVENTION

The invention relates to processes for separating a $C_5$ or $C_6$ alkanediol from a crude product stream comprising the $C_5$ or $C_6$ alkanediol and heavy contaminants comprising one or more of: a $C_{10}$ or $C_{12}$ linear ester, or a $C_{10}$ or $C_{12}$ cyclic acetal or ketal.

In particular, but not exclusively, the invention relates to processes for separating a $C_5$ or $C_6$ alkanediol, from a crude product stream comprising the $C_5$ or $C_6$ alkanediol and heavy contaminants comprising one or more of: a $C_{10}$ or $C_{12}$ linear ester, or a $C_{10}$ or $C_{12}$ cyclic acetal or ketal, wherein the crude product stream further comprises a dialkyl ester of a $C_5$ or $C_6$ di-carboxylic acid or an alkyl ester of a $C_5$ ketoacid.

The invention relates particularly, but not exclusively, to processes for separating 1,6 hexanediol from a crude product stream comprising the 1,6 hexanediol and heavy contaminants comprising one or more of: 6-hydroxyhexyl 6-hydroxyhexanoate and 6-(oxepan-2-yloxy)hexan-1-ol and in particular, but not exclusively, to processes for separating 1,6 hexanediol from a crude product stream comprising the 1,6 hexanediol and heavy contaminants comprising one or more of: 6-hydroxyhexyl 6-hydroxyhexanoate and 6-(oxepan-2-yloxy)hexan-1-ol, wherein the crude product stream further comprises dialkyl adipate and light contaminants.

The invention also relates to processes for producing a $C_5$ or $C_6$ alkanediol from a dialkyl ester of a $C_5$ or $C_6$ di-carboxylic acid or an alkyl ester of a $C_5$ ketoacid and in particular, but not exclusively, to processes for producing 1,6 hexanediol from dialkyl adipate.

BACKGROUND

Whilst several synthetic routes to 1,6-hexanediol are known, one process uses adipic acid as a starting material. The adipic acid is esterified with an alkanol, usually a $C_1$ to $C_4$ alkanol such as methanol, to yield the corresponding dialkyl adipate which is then subjected to hydrogenolysis to yield 1,6-hexanediol and the alkanol, which may be recycled to produce further dialkyl adipate.

Similar processes for producing 1,4 pentanediol using levulinic acid as a starting material and for producing 1,5 pentanediol using glutaric acid as a starting material are also known. Levulinic acid can be esterified to alkyl levulinate, which is the subjected to hydrogenolysis to form 1,4 pentanediol. Glutaric acid can be esterified to dialkyl glutarate, which is the subjected to hydrogenolysis to form 1,5 pentanediol.

The hydrogenolysis also leads to the production of by-products. For example, the hydrogenolysis of the dialkyl adipate, such as dimethyl adipate, may lead to the formation of caprolactone and oxepane. As further examples, the hydrogenolysis of the alkyl levulinate may lead to formation of gamma-valerolactone and 2-methyltetrahydrofuran, and the hydrogenolysis of the dialkyl glutarate may lead to the formation of tetrahydro-2H-pyran-2-one and tetrahydro-2H-pyran. In addition, the hydrogenolysis product mixture will normally contain minor amounts of: the corresponding dialkyl adipate, alkyl levulinate or dialkyl glutarate; the alkanol used for esterification (e.g. methanol); hexanol (when producing a 1,6-hexanediol) or pentanol (when producing a pentanediol); water and other minor impurities.

The various components and product are generally separated and purified by a number of distillation steps using conventional distillation or by use of divided wall columns.

U.S. Pat. Nos. 7,064,239, 6,727,395B1, 6,288,286B1, 6,008,418A and 5,981,769A disclose methods of making 1,6-hexanediol.

U.S. Pat. No. 7,329,330 discloses a divided wall distillation column for the separation and purification of 1,6-hexanediol.

EP2614056B1 discloses methods for producing 1,6-hexanediol and very pure e-caprolactone from a dicarboxylic acid solution (DCL), comprising steps (a) esterification of the DCL with alcohols, (b) partial catalytic hydrogenation of the esters, (c) separation by distillation of 1,6-hexanediol and low-boiling fractions as a top product, and (d) cyclization of the 6-hydroxycaproic acid ester contained in the bottom fraction in the presence of an alcohol boiling at a temperature exceeding the boiling point of caprolactone.

U.S. Pat. No. 8,513,472 discloses a distillation process having 4 steps: a) separating a component having a boiling point lower than that of water and the alcohol used in the esterification from a mixture obtained by the hydrogenation in a first distillation step; b) separating an EV component having a boiling point higher than that of 1,6-hexanediol further in a second distillation step; c) separating an EV component having a boiling point lower than that of 1,6-hexanediol further in a third distillation step; and then d) obtaining 1,6-hexanediol in a fourth distillation step, in this order. U.S. Pat. No. 8,513,472 notes that the inventors have found that when a low-boiling ester value (EV) component including ε-caprolactone or 6-hydroxycaproic acid ester is separated in the third distillation step following the second distillation step, high purity 1,6-hexanediol can be obtained in a high yield. When the order of distillation columns is reversed and a low-boiling EV component such as ε-caprolactone is first separated and removed, a low-boiling EV component such as caprolactone is generated again during separation of a high-boiling EV component in the subsequent distillation column, making it impossible to obtain 1,6-hexanediol having a low ester value. The crude product stream in U.S. Pat. No. 8,513,472 is derived from esterification and hydrogenation of a mixture of carboxylic acids, including glucaric, adipic and 6-hydroxycaproic acid and hence contains $C_5$ species such as 1,5 pentanediol. The distillation system of U.S. Pat. No. 8,513,472 is a chain of columns, with the separation of the EV component having a boiling point lower than that of 1,6-hexanediol happening in the third step of four. A bottom stream largely comprising 1,6-hexanediol and an ester of 1,6-hexanediol with 6-hydroxycaproic acid is recycled from the second step to the hydrogenation.

The applicant has found by experiment that mixtures of 1,6-hexanediol, caprolactone, oxepane, alkanols and water, such as may occur at stages in the production of 1,6-hexanediol by hydrogenolysis of dialkyl adipate, undergo a variety of reactions, which adds difficulty to the problem of distilling these mixtures and obtaining high purity hexanediol by the means described in the prior art. Reactions occur in the hydrogenation steps and further in the distillation steps which produce minor heavy and light components. Examples of these are transesters, e.g. 6 hydroxyhexyl methyl adipate, or heavy ethers.

An important heavy contaminant has been found to be 6-hydroxyhexyl 6-hydroxyhexanoate, which is formed from 1,6-hexanediol and caprolactone. The formation of 6-hydroxyhexyl 6-hydroxyhexanoate is an equilibrium reaction in which the 6-hydroxyhexyl 6-hydroxyhexanoate can revert to hexanediol and caprolactone under certain conditions. Another important heavy contaminant formed is an acetal, 6-(oxepan-2-yloxy)hexan-1-ol, which is heavier than 1,6-hexanediol, but under certain conditions can revert to the aldehyde, 6-hydroxy hexanal, which is lighter than 1,6-hexanediol.

In the production of 1,4 pentanediol, similar reactions can occur which produce 4-hydroxypentyl 4-hydroxypentanoate, which can revert to 1,4 pentanediol and gamma-valerolactone, and/or 5-((2-methyltetrahydrofuran-2-yl)oxy) pentan-2-ol, which can revert to 4-hydroxypentanal. Additionally, 5-hydroxypentan-2-yl 4-hydroxypentanoate may be formed, which can revert to 1,4 pentanediol and gamma-valerolactone. Additionally, 4-((2-methyltetrahydrofuran-2-yl)oxy)pentan-1-ol may be formed, which can also revert to 4-hydroxypentanal. Additionally, 4-((5-methyltetrahydrofuran-2-yl)pentan-lol and/or 5-((5-methyltetrahydrofuran-2yl)oxypentan-2-ol maybe formed, which can revert to 4-oxopentanal.

In the production of 1,5 pentanediol, 5-hydroxypentyl 5-hydroxypentanoate, which can revert to 1,5 pentanediol and tetrahydro-2H-pyran-2-one, and/or 5-((tetrahydro-2H-pyran-2-yl)oxy)pentan-1-ol, which can revert to 5-hydroxypentanal, may be produced.

In prior art distillation systems for the separation of 1,6 hexanediol, these heavy contaminants may fractionate to the bottom of conventional or divided wall columns. In the high temperature and high residence time regions of the column reboiler and sump, the heavy contaminants such as 6-hydroxyhexyl 6-hydroxyhexanoate or 6-(oxepan-2-yloxy) hexan-1-ol react to reform lighter components including caprolactone or 6-hydroxyl hexanal, which can then travel back up the column and contaminate the product if a top or side draw product is taken.

Additionally, 6-hydroxyl hexanal can form in the sump of columns in the presence of oxygen due to the ingress of air in vacuum operated columns. This aldehyde is light and will contaminate the 1,6 hexanediol product for prior art distillation systems arranged with a top or side-draw product off take.

Contamination of the product with caprolactone or 6-hydroxy hexanal can cause quality issues in downstream polymer processes. 6-hydroxy hexanal is also prone to the formation of peroxides, e.g. 7-hydroperoxyoxepan-2-ol or 1-hydroperoxyhexane-1-,6-diol, when in contact with air, which also cause quality issues in the polymer process.

For example, in divided wall arrangements such as those described in U.S. Pat. No. 7,329,330, vapour from the sump of the column contains light components from the reaction of the heavy components in the sump. These light components can travel to the product side of the divided wall and contaminate the product draw with light components. This would not be the case for components in non-reactive mixtures where complete removal of light components from the product draw would normally be expected. While the prior art system of U.S. Pat. No. 8,513,472 proposes a solution to the issue of ε-caprolactone formation in the sump of a column, the straight-through chain of columns in U.S. Pat. No. 8,513,472 may not provide the most cost-effective solution and an efficient overall process.

The applicant has also identified that some of the lighter components, such as esters (including unreacted dialkyl adipate), lactones and aldehydes, which may be treated as Ester Value contaminants by prior art systems, can be further hydrogenated to useful 1,6-hexanediol product, and it would therefore be beneficial to recover those components. However, to do so economically there is a need for an efficient separation of those components from the 1,6-hexanediol product, and from other unusable by-products such as light contaminants. While such a separation could be carried out in a long chain of columns, such schemes may be an expensive solution. A more cost-effective arrangement is needed.

The applicant has identified that similar contamination issues and opportunities can occur in the production of other $C_5$ or $C_6$ alkanediols such as 1,4 pentanediol or 1,5 pentanediol.

There is a continuing need for production of high purity 1,6-hexanediol, and other $C_5$ or $C_6$ alkanediols such as 1,4 pentanediol or 1,5 pentanediol, at low cost. It is thus desirable to provide improved process for the production of $C_5$ or $C_6$ alkanediols, such as 1,6-hexanediol, and particularly processes that reduce losses, increase yields and make efficient use of utilities and feedstocks. There is also a need for improved separation systems for purifying crude $C_5$ or $C_6$ alkanediol streams, such as crude 1,6 hexanediol stream.

SUMMARY OF THE INVENTION

According to a first aspect of the invention there is provided a process for separating a $C_5$ or $C_6$ alkanediol from a crude product stream comprising the $C_5$ or $C_6$ alkanediol, light contaminants and heavy contaminants comprising one or more of: a $C_{10}$ or $C_{12}$ linear ester, or a $C_{10}$ or $C_{12}$ cyclic acetal or ketal, the process comprising feeding the crude product stream to a separation system comprising a first distillation zone, to which the crude product stream is fed and from which the heavy contaminants are removed in a heavies stream taken as a bottom stream, and a second distillation zone, in which the $C_5$ or $C_6$ alkanediol is separated from a reaction product, comprising one or more of: a $C_5$ or $C_6$ cyclic ester, or a $C_5$ or $C_6$ aldehyde, formed in the first distillation zone, and from which the $C_5$ or $C_6$ alkanediol is withdrawn in a refined product stream, characterized in that the reaction product is recovered in a reaction product stream taken as a side draw from either the first distillation zone or the second distillation zone and wherein the light contaminants are removed in a lights stream taken as an overhead stream from either the first distillation zone or the second distillation zone.

The refined product stream is withdrawn from the second distillation zone. Preferably the reaction product stream and the lights stream are taken from the same distillation zone.

Preferably the first and second distillation zones are contained within a single column, the second distillation zone being separated from the first distillation zone by a baffle that starts at the bottom of the column and extends above both a feed point where the crude product stream is fed to the first distillation zone and a withdrawal point where the refined product stream is withdrawn from the second distillation zone. Preferably the reaction product stream is taken as a side draw from above the top of the baffle.

It may be that the first and second distillation zones are in separate columns. Preferably the separate columns comprise a primary column and a secondary column and wherein a first intermediate stream connects an overhead outlet of the secondary column to a side inlet of the primary column and wherein the lights stream is recovered as an overhead stream from the primary column and wherein the reaction product stream is taken from the primary column as a side draw above the side inlet of the primary column. Preferably a second intermediate stream connects a side outlet of the primary column to a side inlet of the secondary column, the side outlet of the primary column being below the side inlet of the primary column to which the first intermediate stream connects. Preferably the primary column comprises a condenser and the secondary column does not comprise a condenser. Preferably the condenser comprised on the primary column is used to vaporize a feed stream used in the production of the $C_5$ or $C_6$ alkanediol, for example an alkanol stream used in an upstream esterification.

Preferably the crude product stream further comprises an unreacted feed material comprising a dialkyl ester of a $C_5$ or $C_6$ di-carboxylic acid or an alkyl ester of a $C_5$ ketoacid, and the unreacted feed material is recovered in the reaction product stream.

Preferably the $C_5$ or $C_6$ alkanediol is a compound according to formula I:

Formula I

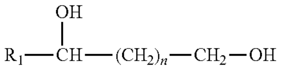

Wherein either $R_1$ is H and n is 3 or 4; or $R_1$ is $CH_3$ and n is 2.

Preferably the $C_{10}$ or $C_{12}$ linear ester is a compound according to formula II:

Formula II

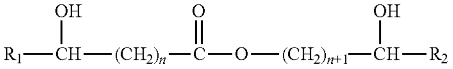

Wherein either $R_1$ and $R_2$ are H and n is 3 or 4; or $R_1$ and $R_2$ are $CH_3$ and n is 2.

Preferably the $C_{10}$ or $C_{12}$ cyclic acetal or ketal is a compound according to Formula III:

Formula III

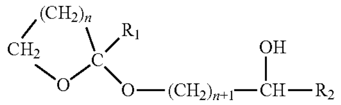

wherein either $R_1$ and $R_2$ are H and n is 3 or 4; or $R_1$ and $R_2$ are $CH_3$ and n is 2.

Preferably the $C_5$ or $C_6$ cyclic ester is a compound according to formula IV:

Formula IV

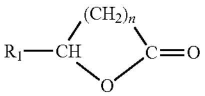

Wherein either $R_1$ and $R_2$ are H and n is 3 or 4; or $R_1$ and $R_2$ are $CH_3$ and n is 2.

Preferably the $C_5$ or $C_6$ aldehyde is a compound according to formula V:

Formula V

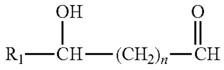

Wherein either $R_1$ is H and n is 3 or 4; or $R_1$ is $CH_3$ and n is 2.

Preferably the unreacted feed material is a compound according to formula VI:

Formula VI

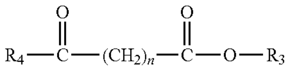

Wherein $R_3$ is a $C_1$ to $C_5$ alkyl group, preferably a $C_1$ to $C_3$ alkyl group and most preferably methyl or ethyl, and wherein either: n is 2 and $R_4$ is $CH_3$; or n is 3 or 4, $R_4$ is $R_5$—O— and $R_5$ is a $C_1$ to $C_5$ alkyl group, preferably a $C_1$ to $C_3$ alkyl group and most preferably methyl or ethyl.

Preferably either:

a) the $C_5$ or $C_6$ alkanediol is 1,6 hexanediol and, where each is present, the $C_{10}$ or $C_{12}$ linear ester is 6-hydroxyhexyl 6-hydroxyhexanoate, the $C_{10}$ or $C_{12}$ cyclic acetal or ketal is 6-(oxepan-2-yloxy)hexan-1-ol, the $C_5$ or $C_6$ cyclic ester is caprolactone, the $C_5$ or $C_6$ aldehyde is 6-hydroxyhexanal, and the unreacted feed material is dialkyl adipate, preferably dimethyl adipate.

b) the $C_5$ or $C_6$ alkanediol is 1,5 pentanediol and, where each is present, the $C_{10}$ or $C_{12}$ linear ester is 5-hydroxypentyl 5-hydroxypentanoate, the $C_{10}$ or $C_{12}$ cyclic acetal or ketal is 5-((tetrahydro-2H-pyran-2-yl)oxy)pentan-1-ol, the $C_5$ or $C_6$ cyclic ester is tetrahydro-2H-pyran-2-one, the $C_5$ or $C_6$ aldehyde is 5-hydroxypentanal, and the unreacted feed material is dialkyl glutarate, preferably dimethyl glutarate.

c) the $C_5$ or $C_6$ alkanediol is 1,4 pentanediol and, where each is present, the $C_{10}$ or $C_{12}$ linear ester is 4-hydroxypentyl 4-hydroxypentanoate, the $C_{10}$ or $C_{12}$ cyclic acetal or ketal is 5-((2-methyltetrahydrofuran-2-yl)oxy)pentan-2-ol, the $C_5$ or $C_6$ cyclic ester is gamma valerolactone, the $C_5$ or $C_6$ aldehyde is 4-hydroxypentanal and the unreacted feed material is alkyl levulinate, preferably methyl levulinate.

The heavy contaminants may additionally comprise $C_{10}$ or $C_{12}$ branched esters, in particular $C_{10}$ branched esters. Such branched esters may occur particularly when the $C_5$ or $C_6$ alkanediol is 1,4 pentanediol, in which case the branched ester may be 5-hydroxypentan-2-yl 4-hydroxypentanoate.

The heavy contaminants may comprise more than one $C_{10}$ or $C_{12}$ cyclic acetal or ketal. In some embodiments the heavy contaminants may comprise both a $C_{10}$ or $C_{12}$ cyclic acetal and a $C_{10}$ or $C_{12}$ cyclic ketal. In some embodiments the heavy contaminants may comprise more than one $C_{10}$ or $C_{12}$ cyclic acetal.

In some embodiments the heavy contaminants may comprise more than one $C_{10}$ or $C_{12}$ cyclic ketal. In some embodiments the heavy contaminants may comprise both more than one $C_{10}$ or $C_{12}$ cyclic acetal and more than one $C_{10}$ or $C_{12}$ cyclic ketal. In particular, when the $C_5$ or $C_6$ alkanediol is 1,4 pentanediol, the heavy contaminants may comprise one or more, two or more, three or more or all four of 5-((2-methyltetrahydrofuran-2-yl)oxy)pentan-2-ol, 4-((2-methyltetrahydrofuran-2-yl)oxy)pentan-1-ol, 4-((5-methyltetrahydrofuran-2-yl)pentan-lol and 5-((5-methyltetrahydrofuran-2yl)oxypentane-2-ol.

Most preferably the $C_5$ or $C_6$ alkanediol is 1,6 hexanediol and, where each is present, the $C_{10}$ or $C_{12}$ linear ester is 6-hydroxyhexyl 6-hydroxyhexanoate, the $C_{10}$ or $C_{12}$ cyclic acetal or ketal is 6-(oxepan-2-yloxy)hexan-1-ol, the $C_5$ or $C_6$ cyclic ester is caprolactone, the $C_5$ or $C_6$ aldehyde is 6-hydroxyhexanal, and the unreacted feed material is dialkyl adipate, preferably dimethyl adipate. In that case, according to a preferable form of the first aspect of the invention, there is provided a process for separating 1,6 hexanediol from a crude product stream comprising the 1,6 hexanediol, light contaminants and heavy contaminants comprising one or more of: 6-hydroxyhexyl 6-hydroxyhexanoate and 6-(oxepan-2-yloxy)hexan-1-ol, the process comprising feeding the crude product stream to a separation system comprising a first distillation zone, to which the crude product stream is fed and from which the heavy contaminants are removed in a heavies stream taken as a bottom stream, and a second distillation zone, in which the 1,6 hexanediol is separated from a reaction product, comprising one or more of caprolactone and 6-hydroxy hexanal, formed in the first distillation zone and from which the 1,6 hexanediol is withdrawn in a refined product stream, characterized in that the reaction product is recovered in a reaction product stream taken as a side draw from either the first distillation zone or the second distillation zone and wherein the light contaminants are removed in a lights stream taken as an overhead stream from either the first distillation zone or the second distillation zone. Preferable and advantageous features of the first aspect of the invention, including those set out above, will now be described in more detail with reference to that process, in which the $C_5$ or $C_6$ alkanediol is 1,6 hexanediol and the other compounds are as listed in (a) above. Such a process may be particularly advantageous because of the particular desirability of a process to produce high purity, low cost 1,6 hexanediol. However, the skilled person, given the information above, will understand how the discussion below may be applied more generally to the first aspect and to process with other $C_5$ or $C_6$ alkanediols and particularly to processes with the compounds set out in (b) and (c) above.

Removing the heavy contaminants in a heavies stream taken as a bottom stream from the first distillation zone, which is the zone to which the crude product stream is fed, advantageously means that reaction products formed by the decomposition of 6-hydroxyhexyl 6-hydroxyhexanoate and 6-(oxepan-2-yloxy)hexan-1-ol in the first distillation zone can be separated from the 1,6-hexanediol in the second distillation zone. Because the 6-hydroxyhexyl 6-hydroxyhexanoate and 6-(oxepan-2-yloxy)hexan-1-ol have already been removed, they are not present to react in the second distillation zone and a high quality 1,6-hexanediol refined product stream can be obtained. Advantageously, the invention also uses the first and second distillation zones to separate light contaminants and the reaction products. The separation of the reaction product stream advantageously means that the lighter components produced in reactions in the first distillation zone that are valuable can be recycled, typically to an upstream hydrogenolysis. By taking the reaction product stream as a side draw from either the first or second distillation zones, that stream can also contain the reaction products from the first distillation zone, which, whilst undesirable in the refined product stream, still have value if recycled upstream in the process. Moreover, recovery of those valuable components is achieved without additional, costly distillation columns.

It will be appreciated that, where the 1,6-hexanediol in the crude product stream is produced from hydrogenolysis of dialkyl adipate, the crude product stream may also comprise unreacted dialkyl adipate. It would be advantageous to recycle that unreacted dialkyl adipate to the hydrogenolysis and particularly advantageous to do so in the reaction product stream so as not to incur the equipment costs of separate recycle streams. Thus, preferably, the crude product stream further comprises dialkyl adipate, and the dialkyl adipate is recovered in the reaction product stream.

Preferably the reaction product stream and the lights stream are taken from the same distillation zone. Thus, the reaction product stream may be taken as a side draw from the first distillation zone and the lights stream taken as an overhead stream from the first distillation zone. The reaction product stream may be taken as a side draw from the second distillation zone and the lights stream be taken as an overhead stream from the second distillation zone. By taking the reaction product stream and the lights stream from the same distillation zone, the two distillation zones can be sized most effectively. In particular, the size, and hence equipment cost, of the distillation zone from which the reaction product stream and the lights stream are not taken can be kept down. Moreover, in some embodiments that distillation zone may be thermally integrated with the other distillation zone, thus saving further equipment costs.

In a particularly preferred arrangement, the first and second distillation zones may be contained within a single column, the second distillation zone being separated from the first distillation zone by a baffle that starts at the bottom of the column and extends above both a feed point where the crude product stream is fed to the first distillation zone and a withdrawal point where the refined product stream is withdrawn from the second distillation zone. Unlike divided wall columns in the prior art, which share the same bottom volume, by providing a baffle that starts at the bottom of the column and extends above both a feed point where the crude product stream is fed to the first distillation zone and a withdrawal point where the refined product stream is withdrawn from the second distillation zone the present invention advantageously prevents contamination of the refined product stream with products formed by the reaction of heavy components that are withdrawn in the heavies stream from the first distillation zone. For example, 6-hydroxyhexyl 6-hydroxyhexanoate and 6-(oxepan-2-yloxy)hexan-1-ol entering in the feed will travel down in the first distillation zone because the baffle extends above the feed point. If the 6-hydroxyhexyl 6-hydroxyhexanoate and the 6-(oxepan-2-yloxy)hexan-1-ol react to form caprolactone and 6-hydroxy hexanal in the bottom of the first distillation zone, the caprolactone and 6-hydroxy hexanal will travel up the first distillation zone to the top of the baffle. Caprolactone and 6-hydroxy hexanal are lighter than 1,6-hexanediol. Thus, as the 1,6-hexanediol travels down the second distillation zone to the withdrawal point where the refined product stream is withdrawn from the second distillation zone, it is not contaminated with caprolactone and 6-hydroxy hexanal in the same way as in prior art divided wall columns where the caprolactone and 6-hydroxy hexanal travel up the column past the withdrawal point for the refined product stream. Preferably the top of the baffle is positioned such that 1,6-hexanediol can pass over the top of the baffle, while 6-hydroxyhexyl 6-hydroxyhexanoate and 6-(oxepan-2-yloxy)hexan-1-ol do not.

Preferably the reaction product stream is taken as a side draw from above the top of the baffle. The applicant has appreciated that the reaction products formed from the 6-hydroxyhexyl 6-hydroxyhexanoate and the 6-(oxepan-2-yloxy)hexan-1-ol, whilst undesirable in the refined product stream, are still valuable if recycled upstream in the process. By taking the reaction product stream as a side draw from above the top of the baffle, components such as caprolactone and 6-hydroxy hexanal formed in the bottom of the first distillation zone can be withdrawn in the reaction product stream. Similarly, if the crude product stream comprises dialkyl adipate, which is also lighter than 1,6-hexanediol, that can also cross the top of the baffle and be withdrawn in the reaction product stream. The reaction product stream is preferably recycled, for example to an upstream hydrogenolysis.

The first and second distillation zones may also advantageously be arranged in separate columns. Preferably the separate columns comprise a primary column and a secondary column and a first intermediate stream connects an overhead outlet of the secondary column to a side inlet of the primary column. The secondary column may thus handle a specific part of the separation, with the lighter components in the secondary column being passed to the primary column for separation. The reaction product stream could be taken from the secondary column, with the lighter components being passed back to the primary column, for example as part of an advantageous integrated reflux for the secondary column, with the lights stream then recovered from the primary column. Preferably however, both the reaction product stream and the lights stream are recovered from the primary column. Thus, the lights stream is preferably recovered as an overhead stream from the primary column and the reaction product stream is preferably taken from the primary column as a side draw above the side inlet of the primary column. Such an arrangement may allow the size and cost of the secondary column, and of the process as a whole, to be reduced because the design and operation of the secondary column can be focused on a particular separation.

For example, the secondary column may be the first distillation zone, with the heavies stream separated from the bottom of the secondary column and the remaining material passed to the primary column for separation of the lights stream, the reaction product stream and the refined product stream. In that way, the size and cost of the secondary column can be kept low and focused on the removal of the heavies stream and, in particular, the reactive 6-hydroxyhexyl 6-hydroxyhexanoate and 6-(oxepan-2-yloxy)hexan-1-ol that are advantageously removed before the separation of the refined product stream in the primary column, which in this embodiment contains the second distillation zone. Such an arrangement provides the advantages of removing the 6-hydroxyhexyl 6-hydroxyhexanoate and the 6-(oxepan-2-yloxy)hexan-1-ol in a first distillation zone, while minimising the cost of the extra column containing that first distillation zone.

Preferably a second intermediate stream connects a side outlet of the primary column to a side inlet of the secondary column, the side outlet of the primary column being below the side inlet of the primary column to which the first intermediate stream connects.

Such a connection between the primary column and the secondary column may be advantageous in several ways. For example, in some embodiments the secondary column may be the second distillation zone. In those embodiments, the heavies stream, lights stream and reaction product stream are preferably taken off in the primary column. Preferably in those embodiments the secondary column processes material from a mid-section of the primary column to separate the refined product stream from lighter components, which are returned to the primary column in the first intermediate stream where they are separated into the reaction product stream and the lights stream. The second intermediate stream advantageously withdraws the material from the mid-section of the primary column for further separation in the secondary column. Such an arrangement may allow the most difficult separation, between the 1,6-hexanediol in the refined product stream and the reaction products, such as 6-hydroxy hexanal or caprolactone, in the reaction product stream, to be carried out in the secondary column designed specifically for that purpose. By returning the overhead stream from the secondary column to the primary column, rather than, for example, withdrawing the reaction product stream from the secondary column, the secondary column does not need to handle the separation of the lights stream from the reaction product stream. The size and operating conditions of the secondary column may thus be able to be optimised to make the separation of the 1,6-hexanediol in the refined product stream and the reaction products as cost-efficient as possible.

Another advantage of the second intermediate stream providing such a connection between the primary column and the secondary column is that there is the potential for beneficial thermal integration between the primary and secondary column. That may be beneficial regardless of whether the first distillation zone is in the primary column and the second distillation zone in the secondary column or vice versa. In particular, the primary column may provide the reflux for the secondary column, thus removing the need for a condenser on the secondary column.

Reducing the equipment count in such a way may advantageously reduce the cost of the process.

Preferably the refined product stream comprises at least 98 wt %; more preferably at least 99 wt %; yet more preferably at least 99.5 wt %; and even more preferably at least 99.9 wt % 1,6-hexanediol.

The crude product stream may comprise from 1 wt % to 20 wt % caprolactone, preferably from 5 wt % to 15 wt % caprolactone. The composition and quantity of the reaction product stream may vary based on factors such as the hydrogenolysis catalyst age, which affects the conversion of dialkyl adipate.

The quantity of the reaction product stream may rise throughout the catalyst life, for example up to about 20 wt % of the plant throughput. Thus, the mass flowrate of the reaction product stream may be in the range of 5 wt % to 30 wt % of the process throughput. Preferably the reaction product stream contains not more than 20 wt % caprolactone, more preferably not more than 15 wt % and most preferably not more than 10 wt %. Preferably the reaction product stream contains at least 1 wt % caprolactone, more preferably at least 2 wt % or at least 5 wt %. Preferably the reaction product stream contains not more than 90 wt %, more preferably not more than 80 wt % dialkyl adipate. Preferably the reaction product stream contains at least 10 wt %, more preferably at least 50 wt % dialkyl adipate. Similar quantities and compositions may apply to the corresponding compounds for processes with other $C_5$ or $C_6$ alkanediols as set out above.

Each of the first distillation zone and the second distillation zone may be operated at a pressure of about 0.05 to about 1 bar absolute, and preferably about 0.05 to about 0.1 bar absolute.

The first and second distillation zones are thus preferably vacuum distillation zones. The first distillation zone is preferably operated at a bottom temperature, i.e. a temperature at the bottom of the first distillation zone, of about 190° C. to about 220° C. The first distillation zone is preferably operated at a top temperature, i.e. a temperature at the top of the first distillation zone, of about 170° C. to about 190° C. The second distillation zone is preferably operated at a bottom temperature of about 180° C. to about 200° C. The second distillation zone is preferably operated at a top temperature of about 80° C. to about 160° C. and more preferably at a top temperature of about 80° C. to 120° C.

The above temperatures for the first and second distillation zones may be particularly advantageous when the alkanediol is 1,6-hexanediol, but may also apply to processes with other $C_5$ or $C_6$ alkanediols as set out above. The first and second distillation zones may be trayed or use structured packing; and preferably use structured packing. The first and second distillation zones may each comprise 10 to 100 theoretical stages, and preferably 15 to 60 theoretical stages.

According to a second aspect of the invention, there is provided a process for producing a $C_5$ or $C_6$ alkanediol from a feed material comprising a dialkyl ester of a $C_5$ or $C_6$ di-carboxylic acid or an alkyl ester of a $C_5$ ketoacid, the process comprising: a hydrogenolysis step in which the feed material undergoes hydrogenolysis to the $C_5$ or $C_6$ alkanediol; and a separation step in which a crude product stream comprising the $C_5$ or $C_6$ alkanediol, light contaminants, and heavy contaminants comprising one or more of: a $C_{10}$ or $C_{12}$ linear ester, or a $C_{10}$ or $C_{12}$ cyclic acetal or ketal, is separated into a heavies stream comprising the heavy contaminants, a refined product stream comprising the $C_5$ or $C_6$ alkanediol, a lights stream comprising the light contaminants, and a reaction product stream comprising a reaction product, comprising one or more of: a $C_5$ or $C_6$ cyclic ester, or a $C_5$ or $C_6$ aldehyde, formed in the separation step, wherein the refined product stream is recovered and the reaction product stream is recycled to the hydrogenolysis step.

It will be appreciated that the separation step of the second aspect of the invention may be carried out in accordance with the first aspect of the invention described above and benefiting from the advantages described above in relation to that first aspect.

Preferably the feed material is produced by esterification of a $C_5$ or $C_6$ di-carboxylic acid or a $C_5$ ketoacid with an alkanol. The alkanol is preferably ethanol or methanol, and most preferably methanol. The alkanol is preferably in the vapour phase for the esterification and that provides opportunities for heat integration with other parts of the process. In particular, the separation step preferably comprises one or more distillation zones having one or more condensers, typically for condensing overhead streams. By feeding liquid alkanol to one or more of those condensers to be vaporised, the heat withdrawn from the overhead stream(s) can be used to vaporise the alkanol. In that way the overall efficiency and heat consumption of the process is improved. Thus, preferably, at least part of the alkanol is vaporised by heat exchange with a hot stream in the separation step. Preferably at least part of the alkanol is vaporised by heat exchange in a condenser in the separation step.

Preferably the $C_5$ or $C_6$ alkanediol is a compound according to formula I:

Formula I

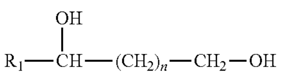

Wherein either $R_1$ is H and n is 3 or 4; or $R_1$ is $CH_3$ and n is 2.

Preferably the $C_{10}$ or $C_{12}$ linear ester is a compound according to formula II:

Formula II

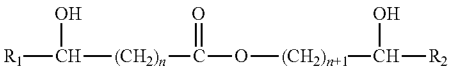

Wherein either $R_1$ and $R_2$ are H and n is 3 or 4; or $R_1$ and $R_2$ are $CH_3$ and n is 2.

Preferably the $C_{10}$ or $C_{12}$ cyclic acetal or ketal is a compound according to Formula III:

Formula III

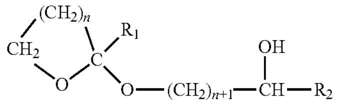

wherein either $R_1$ and $R_2$ are H and n is 3 or 4; or $R_1$ and $R_2$ are $CH_3$ and n is 2.

Preferably the $C_5$ or $C_6$ cyclic ester is a compound according to formula IV:

Formula IV

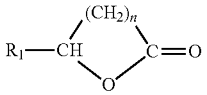

Wherein either $R_1$ and $R_2$ are H and n is 3 or 4; or $R_1$ and $R_2$ are $CH_3$ and n is 2.

Preferably the $C_5$ or $C_6$ aldehyde is a compound according to formula V:

Formula V

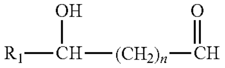

Wherein either $R_1$ is H and n is 3 or 4; or $R_1$ is $CH_3$ and n is 2.

Preferably the feed material is a compound according to formula VI:

Formula VI

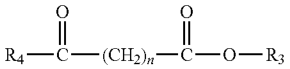

Wherein $R_3$ is a $C_1$ to $C_5$ alkyl group, preferably a $C_1$ to $C_3$ alkyl group and most preferably methyl or ethyl, and wherein either: n is 2 and $R_4$ is $CH_3$; or n is 3 or 4, $R_4$ is $R_5$—O— and $R_5$ is a $C_1$ to $C_5$ alkyl group, preferably a $C_1$ to $C_3$ alkyl group and most preferably methyl or ethyl.

Preferably the $C_5$ or $C_6$ di-carboxylic acid or a $C_5$ ketoacid is a compound according to formula VII:

Formula VII

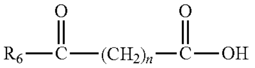

Wherein either $R_6$ is OH and n is 3 or 4, or $R_6$ is $CH_3$ and n is 2.

Preferably either:

a) the $C_5$ or $C_6$ alkanediol is 1,6 hexanediol and, where each is present, the $C_{10}$ or $C_{12}$ linear ester is 6-hydroxyhexyl 6-hydroxyhexanoate, the $C_{10}$ or $C_{12}$ cyclic acetal or ketal is 6-(oxepan-2-yloxy)hexan-1-ol, the $C_5$ or $C_6$ cyclic ester is caprolactone, the $C_5$ or $C_6$ aldehyde is 6-hydroxyhexanal, the feed material is dialkyl adipate, preferably dimethyl adipate, and the $C_5$ or $C_6$ di-carboxylic acid or $C_5$ ketoacid is adipic acid.

b) the $C_5$ or $C_6$ alkanediol is 1,5 pentanediol and, where each is present, the $C_{10}$ or $C_{12}$ linear ester is 5-hydroxypentyl 5-hydroxypentanoate, the $C_{10}$ or $C_{12}$ cyclic acetal or ketal is 5-((tetrahydro-2H-pyran-2-yl)oxy) pentan-1-ol, the $C_5$ or $C_6$ cyclic ester is tetrahydro-2H-pyran-2-one, the $C_5$ or $C_6$ aldehyde is 5-hydroxypentanal, the feed material is dialkyl glutarate, preferably dimethyl glutarate, and the $C_5$ or $C_6$ di-carboxylic acid or $C_5$ ketoacid is glutaric acid.

c) the $C_5$ or $C_6$ alkanediol is 1,4 pentanediol and, where each is present, the $C_{10}$ or $C_{12}$ linear ester is 4-hydroxypentyl 4-hydroxypentanoate, the $C_{10}$ or $C_{12}$ cyclic acetal or ketal is 5-((2-methyltetrahydrofuran-2-yl) oxy)pentan-2-ol, the $C_5$ or $C_6$ cyclic ester is gamma valerolactone, the $C_5$ or $C_6$ aldehyde is 4-hydroxypentanal the feed material is alkyl levulinate, preferably methyl levulinate, and the $C_5$ or $C_6$ di-carboxylic acid or $C_5$ ketoacid is levulinic acid.

Most preferably the $C_5$ or $C_6$ alkanediol is 1,6 hexanediol and, where each is present, the $C_{10}$ or $C_{12}$ linear ester is 6-hydroxyhexyl 6-hydroxyhexanoate, the $C_{10}$ or $C_{12}$ cyclic acetal or ketal is 6-(oxepan-2-yloxy)hexan-1-ol, the $C_5$ or $C_6$ cyclic ester is caprolactone, the $C_5$ or $C_6$ aldehyde is 6-hydroxyhexanal, the feed material is dialkyl adipate, preferably dimethyl adipate, and the $C_5$ or $C_6$ di-carboxylic acid or $C_5$ ketoacid is adipic acid. In that case, according to preferable form of the second aspect of the invention there is provided a process for producing 1,6 hexanediol from dialkyl adipate, the process comprising: a hydrogenolysis step in which the dialkyl adipate undergoes hydrogenolysis to 1,6 hexanediol; and a separation step in which a crude product stream comprising 1,6 hexanediol, light contaminants, and heavy contaminants comprising one or more of: 6-hydroxyhexyl 6-hydroxyhexanoate and 6-(oxepan-2-yloxy)hexan-1-ol, is separated into a heavies stream comprising the heavy contaminants, a refined product stream comprising the 1,6 hexanediol, a lights stream comprising the light contaminants, and a reaction product stream comprising a reaction product, comprising one or more of: caprolactone and 6-hydroxy hexanal, formed in the separation step, wherein the refined product stream is recovered and the reaction product stream is recycled to the hydrogenolysis step. Preferable and advantageous features of the second aspect of the invention, including those set out above, will now be described in more detail with reference to that process, in which the $C_5$ or $C_6$ alkanediol is 1,6 hexanediol and the other compounds are as listed in (a) above. Such a process may be particularly advantageous because of the particular desirability of a process to produce high purity, low cost 1,6 hexanediol. However, the skilled person, given the information above, will understand how the discussion below may be applied more generally to the second aspect to process with other $C_5$ or $C_6$ alkanediols and particularly to processes with the compounds set out in (b) and (c) above.

Such a process advantageously recognises that the reactions occurring in the separation system are not merely an issue to be addressed in producing a high-purity refined product stream, but also an opportunity to recover useful material from the heavy by-products produced in the hydrogenolysis. Recovering and recycling the reaction products advantageously reduces loss from the process, increases efficiency and reduces costs.

Preferably unreacted feed material, such as unreacted dialkyl adipate, in the crude product stream is also recycled in the reaction product stream. The recycling of the unreacted feed material along with useful reaction products from the separation step advantageously recycles all valuable components with a single stream of equipment, thus advantageously reducing the cost of the process.

The separation step preferably comprises one or more distillation zones. Preferably there is an alkanol removal step between the hydrogenolysis step and the separation step. For example, a reactor effluent may be recovered from the hydrogenolysis step and passed to the alkanol removal step. In the alkanol removal step, alkanol, preferably methanol, is removed from the reactor effluent, preferably by distillation. The reactor effluent with the alkanol removed becomes the crude product stream. Preferably 90 wt %, more preferably 95 wt % and yet more preferably 99 wt % of the alkanol is removed from the reactor effluent in the alkanol removal step. Preferably water is also removed from the reactor effluent in the alkanol removal step. Preferably 90 wt %, more preferably 95 wt % and yet more preferably 99 wt % of the water is removed from the reactor effluent in the alkanol removal step.

The provision of a first distillation zone and a second distillation zone in a single column, with the second distillation zone being separated from the first distillation zone by a baffle that starts at the bottom of the column and extends above both a feed point where the crude product stream is fed to the first distillation zone and a withdrawal point where the refined product stream is withdrawn from the second distillation zone is a particularly special and advantageous aspect of the invention in its own right. Such a system may be advantageous in efficiently producing high-purity refined product streams of 1,6-hexanediol, or other $C_5$ or $C_6$ alkanediols, regardless of whether the reaction products from the separation are recovered in a reaction products stream. Thus, according to a third aspect of the invention there may be provided a process for separating a $C_5$ or $C_6$ alkanediol from a crude product stream comprising the $C_5$ or $C_6$ alkanediol and heavy contaminants comprising one or more of: a $C_{10}$ or $C_{12}$ linear ester, or a $C_{10}$ or $C_{12}$ cyclic acetal or ketal, the process comprising feeding the crude product stream to a separation system comprising a first distillation zone, to which the crude product stream is fed and from which the heavy contaminants are removed in a heavies stream taken as a bottom stream, and a second distillation zone, in which the $C_5$ or $C_6$ alkanediol is separated from a reaction product, comprising one or more of a $C_5$ or $C_6$ cyclic ester, or a $C_5$ or $C_6$ aldehyde, formed in the first distillation zone and from which the $C_5$ or $C_6$ alkanediol, preferably 1,6 hexanediol, is withdrawn in a refined product stream, characterized in that the first and second distillation zones are contained within a single column, the second distillation zone being separated from the first distillation zone by a baffle that starts at the bottom of the column and extends above both a feed point where the crude product stream is fed to the first distillation zone and a withdrawal point where the refined product stream is withdrawn from the second distillation zone.

Preferably the $C_5$ or $C_6$ alkanediol is a compound according to formula I:

Formula I

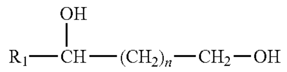

Wherein either $R_1$ is H and n is 3 or 4; or $R_1$ is $CH_3$ and n is 2.

Preferably the $C_{10}$ or $C_{12}$ linear ester is a compound according to formula II:

Formula II

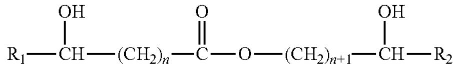

Wherein either $R_1$ and $R_2$ are H and n is 3 or 4; or $R_1$ and $R_2$ are $CH_3$ and n is 2.

Preferably the $C_{10}$ or $C_{12}$ cyclic acetal or ketal is a compound according to Formula III:

Formula III

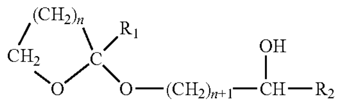

wherein either $R_1$ and $R_2$ are H and n is 3 or 4; or $R_1$ and $R_2$ are $CH_3$ and n is 2.

Preferably the $C_5$ or $C_6$ cyclic ester is a compound according to formula IV:

Formula IV

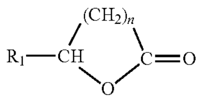

Wherein either $R_1$ and $R_2$ are H and n is 3 or 4; or $R_1$ and $R_2$ are $CH_3$ and n is 2.

Preferably the $C_5$ or $C_6$ aldehyde is a compound according to formula V:

Formula V

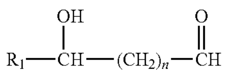

Wherein either $R_1$ is H and n is 3 or 4; or $R_1$ is $CH_3$ and n is 2.

Preferably either:

a) the $C_5$ or $C_6$ alkanediol is 1,6 hexanediol and, where each is present, the $C_{10}$ or $C_{12}$ linear ester is 6-hydroxyhexyl 6-hydroxyhexanoate, the $C_{10}$ or $C_{12}$ cyclic acetal or ketal is 6-(oxepan-2-yloxy)hexan-1-ol, the $C_5$ or $C_6$ cyclic ester is caprolactone, and the $C_5$ or $C_6$ aldehyde is 6-hydroxyhexanal.

b) the $C_5$ or $C_6$ alkanediol is 1,5 pentanediol and, where each is present, the $C_{10}$ or $C_{12}$ linear ester is 5-hydroxypentyl 5-hydroxypentanoate, the $C_{10}$ or $C_{12}$ cyclic acetal or ketal is 5-((tetrahydro-2H-pyran-2-yl)oxy) pentan-1-ol, the $C_5$ or $C_6$ cyclic ester is tetrahydro-2H-pyran-2-one, and the $C_5$ or $C_6$ aldehyde is 5-hydroxypentanal.

c) the $C_5$ or $C_6$ alkanediol is 1,4 pentanediol and, where each is present, the $C_{10}$ or $C_{12}$ linear ester is 4-hydroxypentyl 4-hydroxypentanoate, the $C_{10}$ or $C_{12}$ cyclic acetal or ketal is 5-((2-methyltetrahydrofuran-2-yl) oxy)pentan-2-ol, the $C_5$ or $C_6$ cyclic ester is gamma valerolactone, and the $C_5$ or $C_6$ aldehyde is 4-hydroxypentanal.

Most preferably the $C_5$ or $C_6$ alkanediol is 1,6 hexanediol and, where each is present, the $C_{10}$ or $C_{12}$ linear ester is 6-hydroxyhexyl 6-hydroxyhexanoate, the $C_{10}$ or $C_{12}$ cyclic acetal or ketal is 6-(oxepan-2-yloxy)hexan-1-ol, the $C_5$ or $C_6$ cyclic ester is caprolactone, and the $C_5$ or $C_6$ aldehyde is 6-hydroxyhexanal. In that case, according to a preferable form of the third aspect of the invention there is provided a process for separating 1,6 hexanediol from a crude product stream comprising the 1,6 hexanediol and heavy contaminants comprising one or more of: 6-hydroxyhexyl 6-hydroxyhexanoate and 6-(oxepan-2-yloxy)hexan-1-ol, the process comprising feeding the crude product stream to a separation system comprising a first distillation zone, to which the crude product stream is fed and from which the heavy contaminants are removed in a heavies stream taken as a bottom stream, and a second distillation zone, in which the 1,6 hexanediol is separated from a reaction product, comprising one or more of caprolactone and 6-hydroxy hexanal, formed in the first distillation zone and from which the 1,6 hexanediol is withdrawn in a refined product stream, characterized in that the first and second distillation zones are contained within a single column, the second distillation zone being separated from the first distillation zone by a baffle that starts at the bottom of the column and extends above both a feed point where the crude product stream is fed to the first distillation zone and a withdrawal point where the refined product stream is withdrawn from the second distillation zone. Preferable and advantageous features of the third aspect of the invention, including those set out above, will now be described in more detail with reference to that process, in which the $C_5$ or $C_6$ alkanediol is 1,6 hexanediol and the other compounds are as listed in (a) above. Such a process may be particularly advantageous because of the particular desirability of a process to produce high purity, low cost 1,6 hexanediol. However, the skilled person, given the information above, will understand how the discussion below may be applied to more generally to the third aspect and to process with other $C_5$ or $C_6$ alkanediols and particularly to processes with the compounds set out in (b) and (c) above.

Combining the first and second distillation zones into a single column advantageously removes many of the costs associated with separate columns. There is only one column to produce, transport and install, connections between separate columns are not required and the two distillation zones are thermally integrated with one another. These advantages may be particularly realised in the purification of crude product streams comprising 1,6-hexanediol because the most difficult separation is the separation between the 1,6-hexanediol and the components like caprolactone and 6-hydroxy hexanal that are undesirable in the refined product stream. The separation of the 6-hydroxyhexyl 6-hydroxyhexanoate and the 6-(oxepan-2-yloxy)hexan-1-ol from the 1,6-hexanediol in the bottom of the column is more straightforward and this means that there is space to divide the lower part of the column in two with the baffle and include the second distillation zone in the lower part of the column without significantly increasing the size of the column. The first and second distillation zones may therefore in this case be provided in a column of similar size as would be needed to house the first distillation zone alone. It will be appreciated that such an arrangement can advantageously lead to cost savings. Unlike divided wall columns in the prior art, which share the same bottom volume, by providing a baffle that starts at the bottom of the column and extends above both a feed point where the crude product stream is fed to the first distillation zone and a withdrawal point where the refined product stream is withdrawn from the second distillation zone the present invention advantageously secures the benefits of containing the first and second distillation zone in a single column while also preventing contamination of the refined product stream with products formed by the reaction of heavy components that are withdrawn in the heavies stream from the first distillation zone. For example, 6-hydroxyhexyl 6-hydroxyhexanoate and 6-(oxepan-2-yloxy)hexan-1-ol entering in the feed will travel down in the first distillation zone because the baffle extends above the feed point. If the 6-hydroxyhexyl 6-hydroxyhexanoate and the 6-(oxepan-2-yloxy)hexan-1-ol react to form caprolactone and 6-hydroxy hexanal in the bottom of the first distillation zone, the caprolactone and 6-hydroxy hexanal will travel up the first distillation zone to the top of the baffle. Caprolactone and 6-hydroxy hexanal are lighter than 1,6-hexanediol. Thus, as the 1,6-hexanediol travels down the second distillation zone to the withdrawal point where the refined product stream is withdrawn from the second distillation zone, it is not contaminated with caprolactone and 6-hydroxy hexanal in the same way as in prior art divided wall columns where the caprolactone and 6-hydroxy hexanal travel up the column past the withdrawal point for the refined product stream. Preferably the top of the baffle is positioned such that 1,6-hexanediol can pass over the top of the baffle, while 6-hydroxyhexyl 6-hydroxyhexanoate and 6-(oxepan-2-yloxy)hexan-1-ol do not.

The single column preferably comprises two reboilers, one connected to the first distillation zone and one connected to the second distillation zone. The provision of two reboilers may advantageously allow independent control of the bottom temperature of the first and second distillation zone.

The skilled person will appreciate that features of the invention described in relation to one aspect of the invention may be equally applicable to another aspect of the invention. For example, it will be appreciated that the advantages described above in relation to the third aspect of the invention may apply equally to the use of the third aspect of the invention in its own right or to the use of the third aspect of the invention in the first or second aspects of the invention. It will be appreciated that some features of the invention may not be applicable to, and may be excluded from, some aspects of the invention.

DESCRIPTION OF THE DRAWINGS

The present invention will now be described, by way of example, with reference to the following figures, of which.

DETAILED DESCRIPTION

Figure 1:
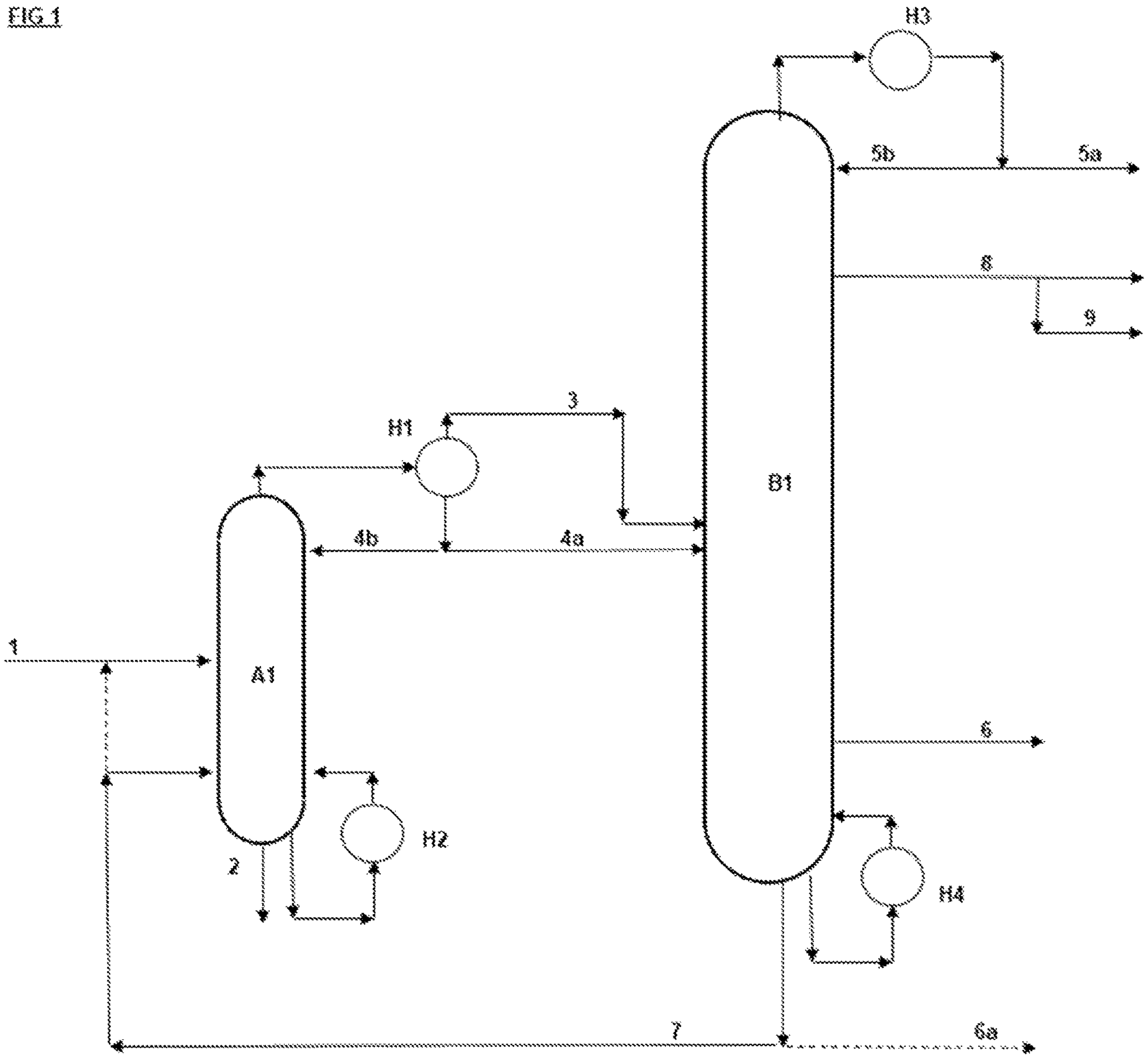
FIG. 1 shows a process according to aspects of the present invention.

In FIG. 1 a crude product stream 1 is fed to a first distillation zone A1 comprised in a secondary column. The crude product stream 1 comprises a mixture including hexanediol, caprolactone, oxepane, dimethyl adipate, hexanol, methyl-hydroxyhexanoate, transesters (e.g. 6 hydroxyhexyl methyl adipate), ethers (e.g. hydroxyhexyl-methyl ether or other heavy ethers), 6-hydroxyhexyl 6-hydroxyhexanoate, 6-(oxepan-2-yloxy)hexan-1-ol, 6-hydroxy hexanol, other minor impurities, and light contaminants such as residual alkanols, and/or water. In some embodiments, a recycle stream 7 containing heavy components from a second distillation zone B1, comprised in a separate, primary column, may also be fed to the first distillation zone A1, preferably at the same feed point or further down the first distillation zone A1. The heavy components from the crude product stream 1 and recycle stream 7 concentrate in the lower section of the first distillation zone A1 and are removed in a heavies stream 2. First distillation zone A1 comprises a reboiler H2.

The heavy components include the 6-hydroxyhexyl 6-hydroxyhexanoate which reacts in the sump of first distillation zone A1 to form 1,6-hexanediol, and caprolactone. 6-(oxepan-2-yloxy)hexan-1-ol also reacts in the sump to form 6-hydroxy hexanal and further 6-hydroxy hexanal is formed in the presence of oxygen due to the ingress of air into the first distillation zone A1. The caprolactone and 6-hydroxy hexanal, being lighter, will then travel back up the first distillation zone A1. Heavy components, including 6-hydroxyhexyl 6-hydroxyhexanoate and 6-(oxepan-2-yloxy)hexan-1-ol will reduce in composition in the upper section of first distillation zone A1, reducing the heavy component content in the overhead vapour draw 3 and/or overhead liquid draw 4*a*. Overhead vapour draw 3 and overhead liquid draw 4*a* are examples of first intermediate streams connecting an overhead outlet of the secondary column comprising first distillation zone A1 with a side inlet of the primary column comprising second distillation zone B1. A condenser H1 is provided at the top of first distillation zone A1 and can be a partial or full condenser to provide reflux return 4*b* to first distillation zone A1. If condenser H1 is a partial condenser, overhead vapour draw 3 is fed to a second distillation zone B1. An overhead liquid draw 4*a* may also be passed to second distillation zone B1 in that case. If condenser H1 is a full condenser then there will be no overhead vapour draw 3 and overhead liquid draw 4*a* will be fed to the second distillation zone B1. The condenser H1 can be cooled conventionally by cooling water or by usefully recovering heat for the overall process for example by raising steam or evaporating an alkanol, such as methanol, fed to the process. Caprolactone and 6-hydroxy hexanol, from reaction of 6-hydroxyhexyl 6-hydroxyhexanoate and 6-(oxepan-2-yloxy)hexan-1-ol in the sump will appear in the overhead vapour draw 3 and/or the overhead liquid draw 4*a*. Other lighter components, e.g. dimethyl adipate, methyl-hydroxyhexanoate, hydroxyhexyl-methyl ether, hexanol, residual alkanols, oxepane and water from the feed will also appear in the overhead vapour draw 3 and/or the overhead liquid draw 4*a*.

Second distillation zone B1 comprises a condenser H3 which provides reflux 5*b* to distillation zone B. The condenser H3 can be cooled conventionally by cooling water or by usefully recovering heat for the overall process for example by raising steam or evaporating an alkanol, such as methanol, fed to the process. Second distillation zone B1 further comprises a reboiler H4. The 1,6-hexanediol can be recovered as a side-draw refined product stream 6 or a bottom refined product stream 6*a* from the bottom section of second distillation zone B1. By this combination the light and heavy components in the crude product stream 1 and the light components produced by reaction in the sump of first distillation zone A1 are removed and reduced in composition in refined product stream 6 or 6*a*. If a bottom refined product stream 6*a* is taken, any further aldehyde formed in the presence of oxygen due to the ingress of air into the sump of second distillation zone B1, which is light compared to the product 1,6-hexanediol, will travel up second distillation zone B1 reducing the propensity to contaminate the bottom refined product stream 6*a*. If a side refined product stream 6 is taken then a purge of heavies 7 can be recycled to first distillation zone A1. Taking a side draw refined product stream 6 will also reduce any heavies contamination of the refined product stream 6 if further heavy components are made in the sump of second distillation zone B1. The lighter components are concentrated in the upper sections of second distillation zone B1. The light contaminants are removed in the lights stream 5*a*. A reaction product stream 8, which include the esters dimethyl adipate and methyl-hydroxyhexanoate, and reaction products from the first distillation zone such as caprolactone and 6-hydroxy hexanal, is recovered as a side draw from second distillation zone B1. The reaction product stream can be recycled to a hydrogenolysis step in the overall 1,6-hexanediol production process, to produce more 1,6-hexanediol. Adjustment of the lights stream 5*a* will maximise the removal of the light contaminants and minimise the loss of esters, caprolactone and aldehyde. This provides an efficient recycle and hydrogenation of the unconverted ester material and reaction products from the first distillation zone A1, which improves the efficiency of the 1,6-hexanediol production. A purge 9 can be taken from the reaction product stream 8 to remove other intermediate boilers which cannot be converted to 1,6-hexanediol and would otherwise contaminate the 1,6-hexanediol product.

Figure 2:
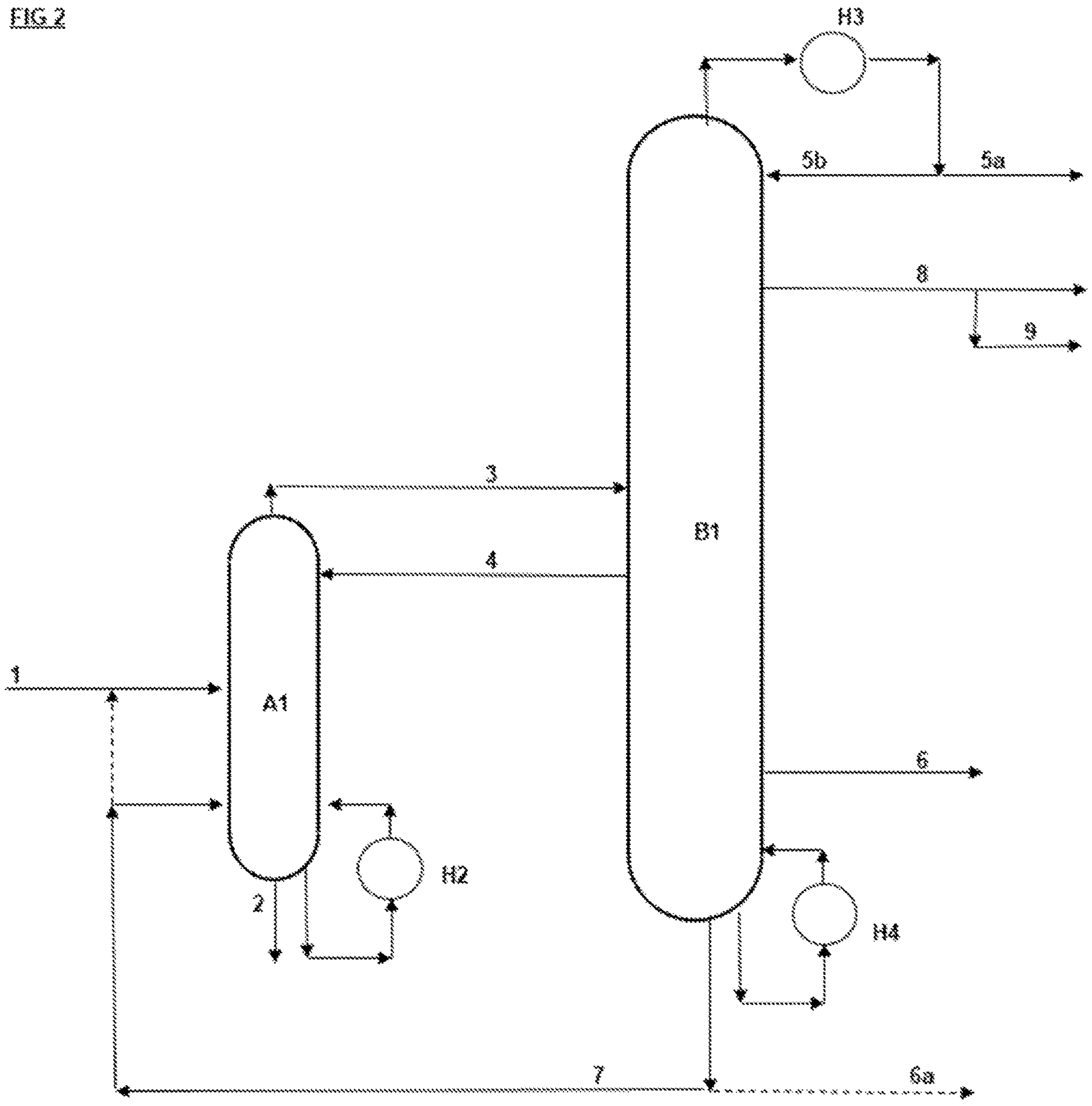
FIG. 2 shows a process according to aspects of the present invention.

In FIG. 2, in which like items are like numbered and not described again, a thermally integrated arrangement of the secondary column comprising first distillation zone A1 and the primary column comprising second distillation zone B1 is used. The duties of condensers H1 and H3 in FIG. 1 can be combined in condenser H3 in FIG. 2, saving on the number of installed equipment items. Overhead vapour draw 3 from first distillation zone A1 is a first intermediate stream connecting an overhead outlet of the secondary column with a side inlet of the primary column. A liquid side draw 4 is taken from second distillation zone B1 and to provide reflux to first distillation zone A1. Liquid side draw 4 is thus a second intermediate stream connecting a side outlet of the primary column to a side inlet of the secondary column, the side outlet of the primary column being below the side inlet of the primary column to which the first intermediate stream, overhead vapour stream 3, connects.

Figure 3:
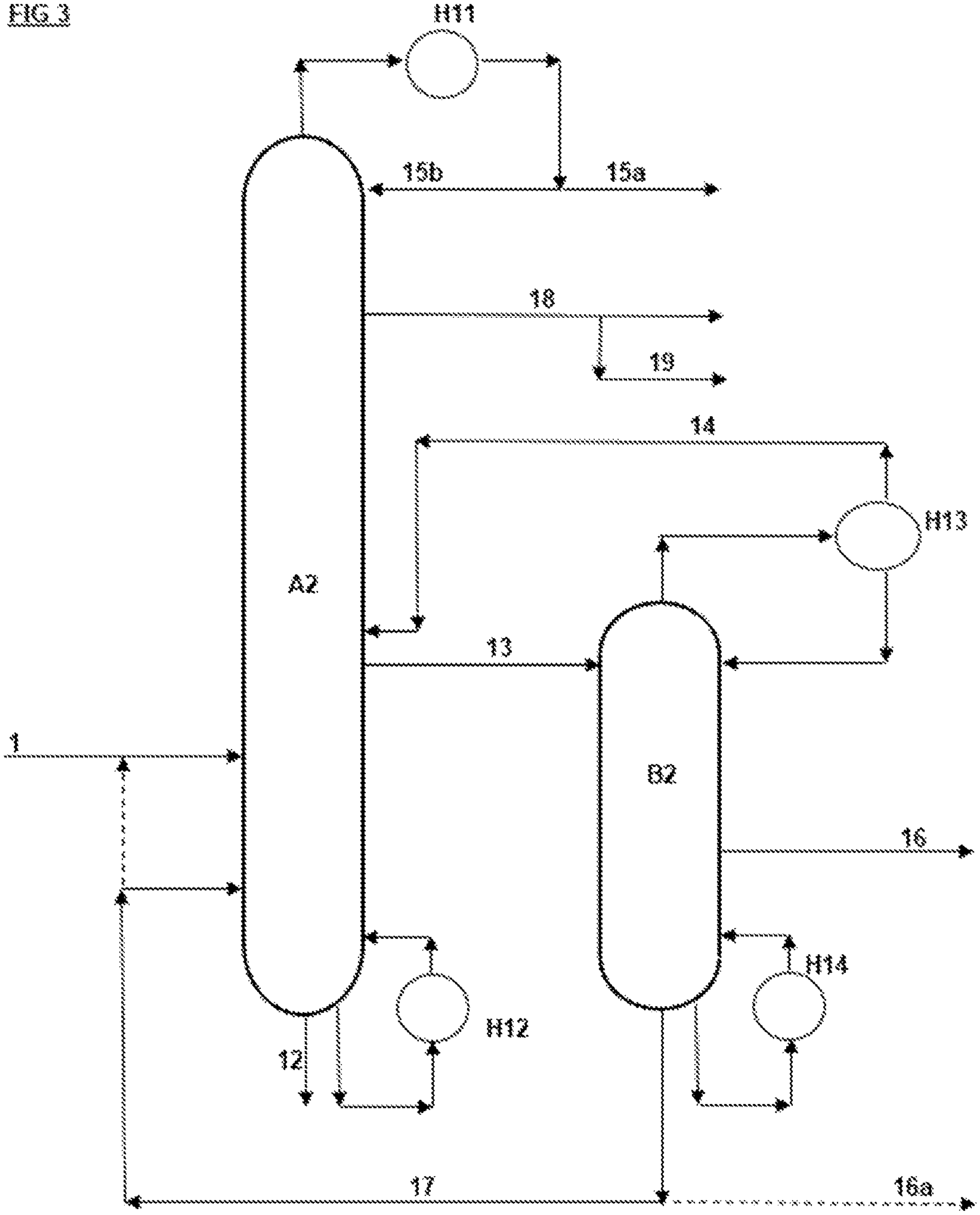
FIG. 3 shows a process according to aspects of the present invention.

In FIG. 3 the crude product stream 1 having the same composition as in FIGS. 1 and 2 is fed to a first distillation zone A2 comprised in a primary column. In some embodiments, a recycle stream 17 containing heavy components from a second distillation zone B2, comprised in a separate, secondary column, may also be fed to the first distillation zone A2, preferably at the same feed point or further down the first distillation zone A2. The heavy components from the crude product stream 1 and recycle stream 17 concentrate in the lower section of the first distillation zone A2 and are removed in a heavies stream 12. First distillation zone A2 comprises a reboiler H12.

As above, the heavy components include the 6-hydroxyhexyl 6-hydroxyhexanoate which reacts in the sump of first distillation zone A2 to form 1,6-hexanediol, and caprolactone. 6-(oxepan-2-yloxy)hexan-1-ol also reacts in the sump to form further 6-hydroxy hexanal and further 6-hydroxy hexanal is formed in the presence of oxygen due to the ingress of air into the first distillation zone A2. The caprolactone and 6-hydroxy hexanal, being lighter, will then travel back up the first distillation zone A2. Heavy components, including 6-hydroxyhexyl 6-hydroxyhexanoate and 6-(oxepan-2-yloxy)hexan-1-ol will reduce in composition above the feed point of the crude product stream 1 into first distillation zone A2, reducing the heavy component content in the side draw 13. Side draw 13 is a second intermediate stream connecting a side outlet of the primary column to a side inlet of the secondary column. A condenser H11 is provided at the top of first distillation zone A2 to provide reflux 15*b* to the first distillation zone A2. The condenser H11 can be cooled conventionally by cooling water or by usefully recovering heat for the overall process for example by raising steam or evaporating an alkanol, such as methanol, fed to the process. Caprolactone and 6-hydroxy hexanal, from reaction of 6-hydroxyhexyl 6-hydroxyhexanoate and 6-(oxepan-2-yloxy)hexan-1-ol in the sump will appear in the side draw 13. This side draw 13 may be taken from above the feed point of the crude product stream 1. Other light components (e.g. dimethyl adipate), methyl-hydroxyhexanoate, hydroxyhexyl-methyl ether, hexanol, oxepane and light contaminants such as residual alkanols, and water from the crude product stream 1 may also appear in the side draw 13. These will be removed in a second distillation zone B2 and returned to the first distillation zone A2 via first intermediate stream 14, which connects an overhead outlet of the secondary column comprising second distillation zone B2 to a side inlet of the primary column comprising first distillation zone A2. The side outlet from which side-draw 13 is taken is below the side inlet to which first intermediate stream 14 is fed. Reflux for the second distillation unit B2 may be provided by a partial condenser H13. The product 1,6-hexanediol can be taken as a side-draw refined product stream 16 or a bottom refined product stream 16*a*. Second distillation zone B2 comprises a reboiler H14.

By this process, the light and heavy components in the feed 1 and the light components produced by reaction in the sump of the first distillation zone A2 are removed and reduced in composition in the refined product stream 16 or 16*a*. If a side refined product stream 16 is taken, then a purge of heavies can be recycled by recycle stream 17 to the first distillation zone A2. The light components are concentrated in the upper sections of the first distillation zone A2. The light contaminants are removed in the overhead lights stream 15*a*. A reaction product stream 18 is removed as a side draw from first distillation zone A2. The reaction product stream 18 include the esters, dimethyl adipate and methyl-hydroxyhexanoate, and reaction products from the sump of the first distillation zone A2 such as caprolactone, which can be recycled to hydrogenation in the overall 1,6-hexanediol production process, to produce more 1,6-hexanediol. A purge 19 can be taken from the reaction product stream 18 to remove other intermediate boilers which cannot be converted to 1,6-hexanediol and would otherwise contaminate the refined product stream 16 or 16*a*.

Figure 4:
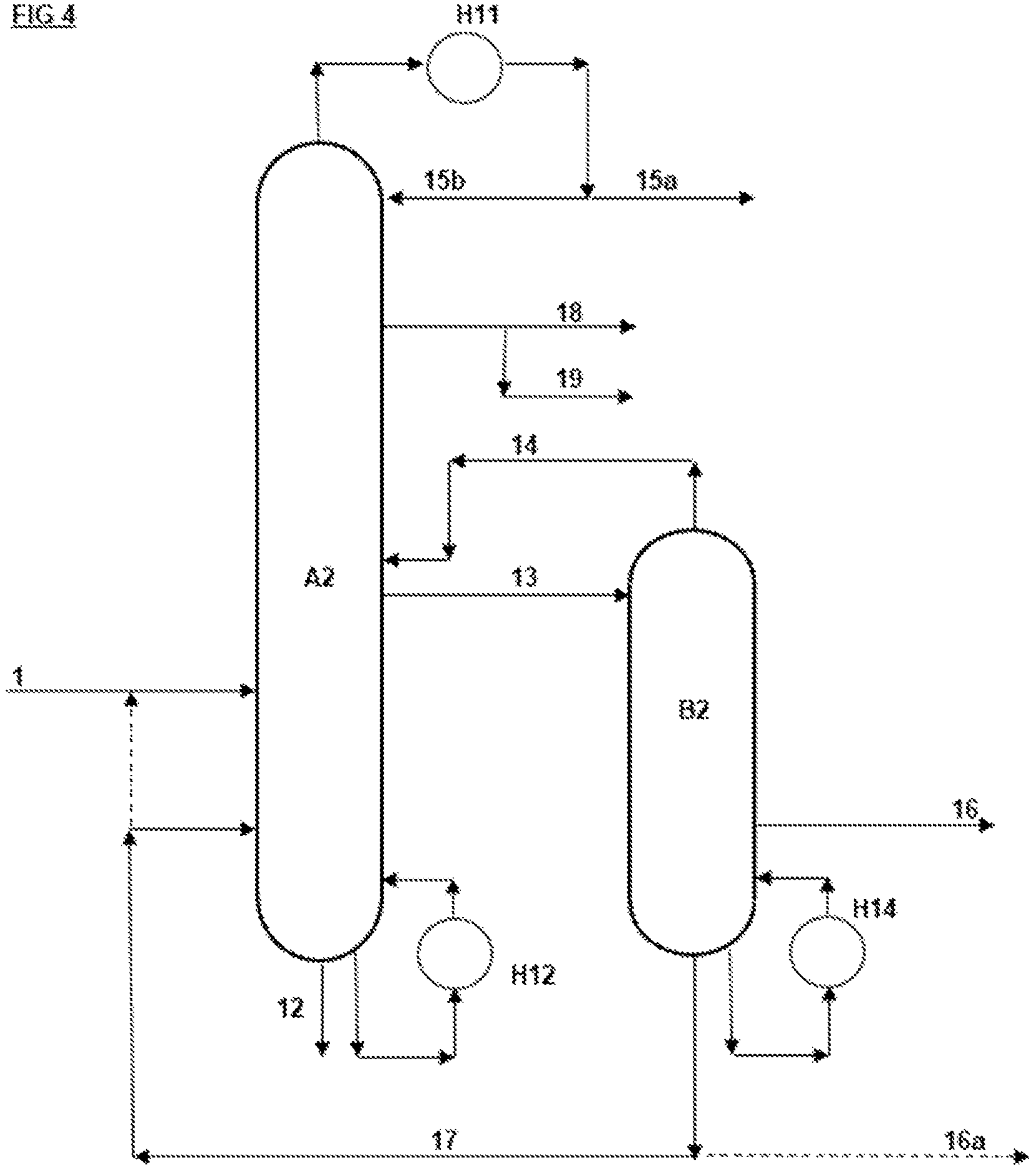
FIG. 4 shows a process according to aspects of the present invention.

In FIG. 4, in which like items are like numbered and not described again, a thermally integrated arrangement of the primary column comprising first distillation zone A2 and the secondary column comprising second distillation zone B2 is used. The duties of condensers H11 and H13 in FIG. 3 can be combined in condenser H11 in FIG. 4, saving on the number of installed equipment items. The condenser H11 can be cooled conventionally by cooling water or by usefully recovering heat for the overall process for example by raising steam or evaporating an alkanol, such as methanol, fed to the process. Side draw 13 from first distillation zone A2 is a second intermediate stream connecting a side outlet of the primary column to a side inlet of the secondary column. First intermediate stream 14 connects an overhead outlet of the secondary column comprising the second distillation zone B2 with a side inlet of the primary column comprising the first distillation zone A2. The side outlet of the primary column is below the side inlet of the primary column to which the first intermediate stream 14 connects. In this embodiment, the secondary column comprising the second distillation zone B2 effectively acts as an extra distillation zone for material from a mid-section of the primary column comprising first distillation zone A2. That material is withdrawn in side draw 13, and is separated in second distillation zone B2, which focuses on the most difficult separation between the refined product stream 16, 16*a* and the reaction product stream 18, with any light contaminants and the reaction products being returned to the first distillation zone A2 by first intermediate stream 14 to be separated and recovered in the lights stream 15*a* and the reaction product stream 18 and with the refined product stream 16 or 16*a* being recovered from the second distillation zone B2.

Figure 5:
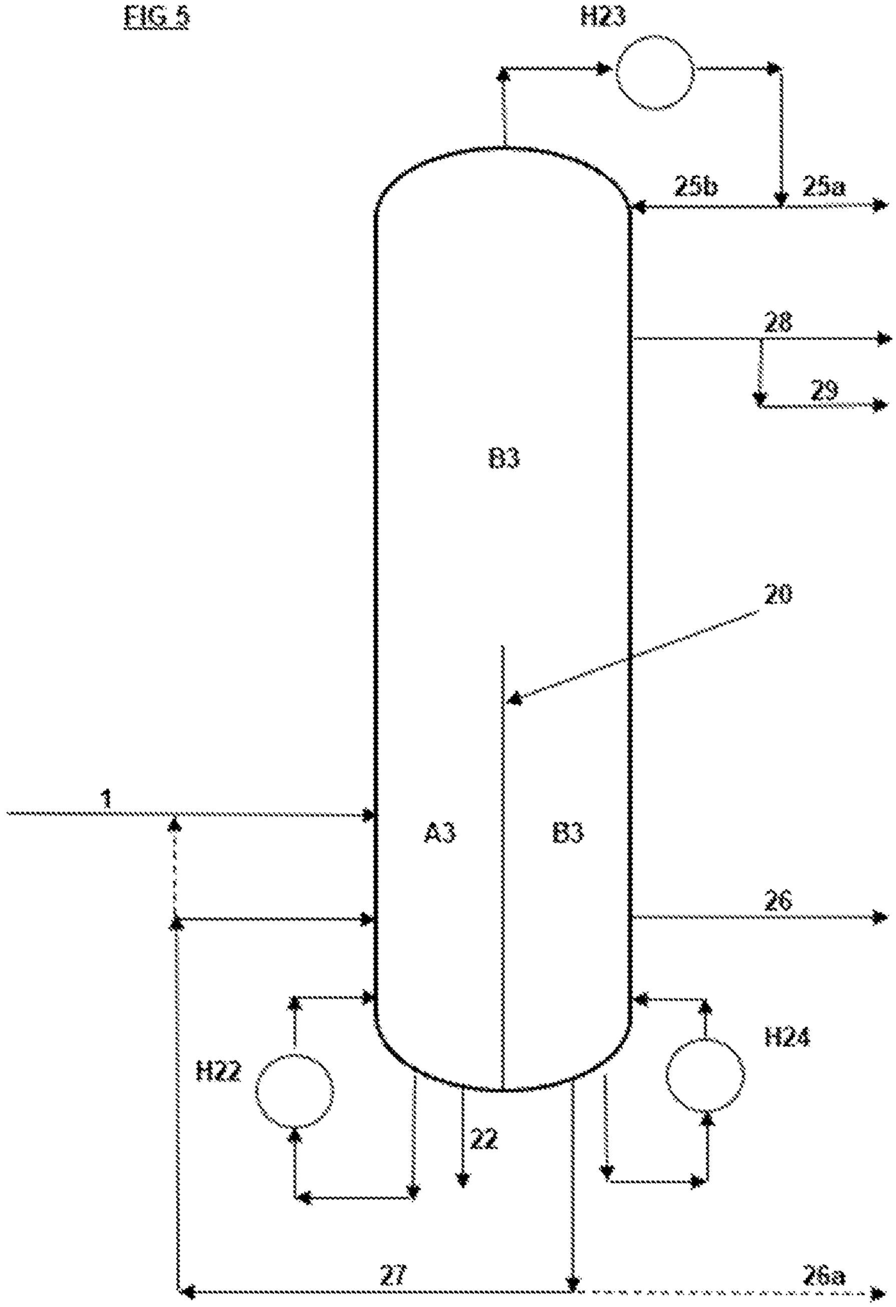
FIG. 5 shows a process according to aspects of the present invention.

FIG. 5 shows an alternative arrangement of a first distillation zone A3 and second distillation zone B3. As shown in FIG. 5, the first distillation zone A3 and the second distillation zone B3 may advantageously be combined into a single column by use of a sealed, separating baffle 20 which extends completely to the bottom of the column. The baffle 20 extends up the column to a point above the feed point to the first distillation zone A3 of the crude product stream 1, which has the same composition as in the previous Figures. The baffle 20 also extends above the withdrawal point of the refined product stream 26, 26*a* from the second distillation zone B3. The single column comprises two reboilers H22 and H24. Heavies stream 22 is withdrawn from the bottom of first distillation zone A3, while, particularly if the refined product stream 26 is taken as a side draw, a heavy purge stream 27 may be recycled from second distillation zone B3 back to the first distillation zone A3 either at or below the feed point of the crude product stream 1. Alternatively of additionally, refined product stream 26*a* may be taken as a bottom stream. The advantages of refined product streams 26 and 26*a* are as discussed above in relation to refined product stream 6 and 6*a*. Indeed, the operation of FIG. 5 in terms of separation is very similar to the operation of FIGS. 1 and 2, with FIG. 5 benefiting from being a single column and being fully thermally integrated. Thus, the reaction products from the sump of first distillation zone A3 are recovered in reaction product stream 28, with a possible purge 29, in the same way as reaction product stream 8. The light contaminants are withdrawn in lights stream 25*a* in the same way as lights stream 5*a*, with a reflux 25*b* being provided by condenser H23 as it is with reflux 5*b* and condenser H3. High 1,6-hexanediol purity is obtained in the refined product stream 26, 26*a* because the reaction products rise up the baffle 20 and then continue to rise in second distillation zone B3 until they are removed in the reaction product stream 28. Thus, they do not drop down second distillation zone B3 and contaminate the refined product streams 26, 26*a*. Combining the first distillation zone A3 and the second distillation zone B3 into a single column as in FIG. 5 is particularly advantageous for the separations described herein because the duty of first distillation zone A3 and the duty of the lower section of second distillation zone B3 combined (and separated by baffle 20) require a column diameter similar to the diameter required by the upper section of second distillation zone B3 above the baffle 20. Hence combining the duties in a single column requires a column similar in size to that of the primary column comprising second distillation zone B1 in FIG. 1 or FIG. 2, resulting in a significant saving in equipment costs.

Figure 6:
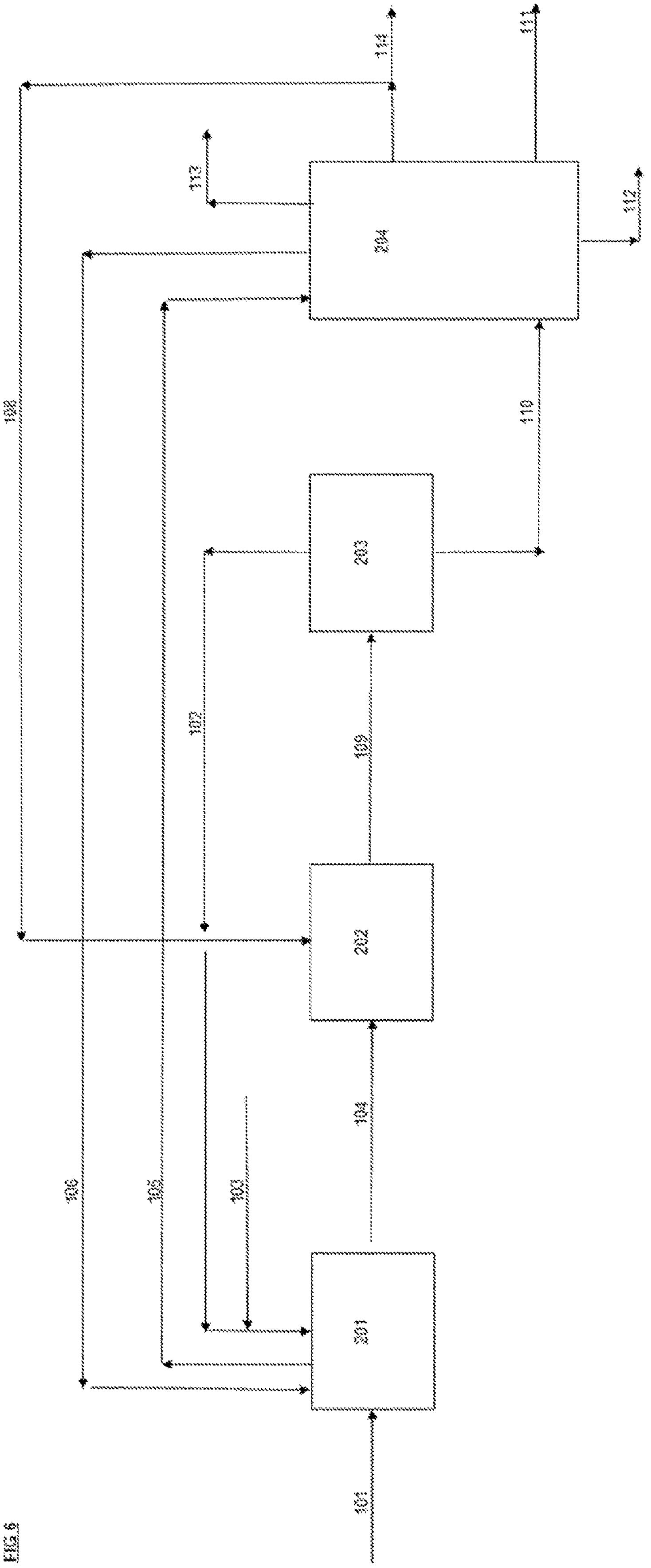
FIG. 6 shows a process according to aspects of the present invention.

In FIG. 6 adipic acid 101 is fed to an esterification unit 201 and esterified with alkanol, such as methanol. The alkanol comprises recycled alkanol 102 from a downstream alkanol and water removal step 203 and make up alkanol 103. The product of the esterification unit 201 comprises dialkyl adipate 104. The alkanol used in the esterification unit 201 can be vaporised using heat from the product separation process 204, for example a process according to the first or third aspects of the invention or as described in relation to FIGS. 1 to 5 above.

The product separation process 204 thus comprises distillation zones as described above and the heat from those distillation zones, can be used to vaporise liquid alkanol 105. For example, liquid alkanol may be fed to a condenser, such as condenser H1, H3 or H11 in FIGS. 1 to 5 above where it can be subjected to heat exchange with the stream passing through the condenser to cool that stream and vaporise the liquid alkanol 105, which can then be fed back to the esterification unit 201 as alkanol vapour 106. Dialkyl adipate 104 is fed to hydrogenation 202 with recycled ester 108 and those are hydrogenated to 1,6 hexanediol which is withdrawn in reactor effluent 109. Alkanol and water are removed by distillation in alkanol and water removal step 203 and the remaining crude product stream 110 fed to the product separation process 204. As described above in relation to FIGS. 1 to 5, in the separation process 204 the crude product stream 110 is separated into a refined product stream (111) comprising the 1,6 hexanediol, heavies stream (112), lights stream 113 and reaction product stream 108, which may comprise esters and/or caprolactone and 6-hydroxy hexanal formed in the product separation process 204. A purge 114 can be taken from the reaction product stream 108.

While the embodiments above relate to examples wherein the $C_5$ or $C_6$ alkanediol is 1,6 hexanediol and, where each is present, the $C_{10}$ or $C_{12}$ linear ester is 6-hydroxyhexyl 6-hydroxyhexanoate, the $C_{10}$ or $C_{12}$ cyclic acetal or ketal is 6-(oxepan-2-yloxy)hexan-1-ol, the $C_5$ or $C_6$ cyclic ester is caprolactone, the $C_5$ or $C_6$ aldehyde is 6-hydroxyhexanal, the feed material or unreacted feed material is dialkyl adipate, preferably dimethyl adipate, and the $C_5$ or $C_6$ di-carboxylic acid or $C_5$ ketoacid is adipic acid the skilled person will appreciate, given the teaching elsewhere in this document, how to apply the features of those examples in processes with other $C_5$ and $C_6$ alkanediols and their corresponding compounds as described elsewhere in this document.

It will be appreciated by those skilled in the art that the above embodiments are described by way of example only and that alterations and modifications are possible within the scope of the invention. For example, the single column arrangement of FIG. 5 is advantageous even if the reaction product stream 28 is not collected separately from the lights stream 25*a*.

The invention claimed is:

1. A process for separating a $C_5$ or $C_6$ alkanediol from a crude product stream comprising the $C_5$ or $C_6$ alkanediol, light contaminants and heavy contaminants comprising one or more of a $C_{10}$ or $C_{12}$ linear ester, or a $C_{10}$ or $C_{12}$ cyclic acetal or ketal, the process comprising:

feeding the crude product stream to a separation system comprising a first distillation zone, to which the crude product stream is fed and from which the heavy contaminants are removed in a heavies stream taken as a bottom stream, and a second distillation zone, in which the $C_5$ or $C_6$ alkanediol is separated from a reaction product, comprising one or more of: a $C_5$ or $C_6$ cyclic ester, or a $C_5$ or $C_6$ aldehyde, formed in the first distillation zone and from which the $C_5$ or $C_6$ alkanediol is withdrawn in a refined product stream, wherein the reaction product is recovered in a reaction product stream taken as a side draw from either the first distillation zone or the second distillation zone and wherein the light contaminants are removed in a lights stream taken as an overhead stream from either the first distillation zone or the second distillation zone.

2. The process according to claim 1, wherein the reaction product stream and the lights stream are taken from the same distillation zone.

3. The process according to claim 1 wherein the first and second distillation zones are contained within a single column, the second distillation zone being separated from the first distillation zone by a baffle that starts at the bottom of the column and extends above both a feed point where the crude product stream is fed to the first distillation zone and a withdrawal point where the refined product stream is withdrawn from the second distillation zone.

4. The process according to claim 3, wherein the reaction product stream is taken as a side draw from above the top of the baffle.

5. The process according to claim 1, wherein the first and second distillation zones are in separate columns.

6. The process according to claim 5 wherein the separate columns comprise a primary column and a secondary column and wherein a first intermediate stream connects an overhead outlet of the secondary column to a side inlet of the primary column and wherein the lights stream is recovered as an overhead stream from the primary column and wherein the reaction product stream is taken from the primary column as a side draw above the side inlet of the primary column.

7. The process according to claim 6, wherein a second intermediate stream connects a side outlet of the primary column to a side inlet of the secondary column, the side outlet of the primary column being below the side inlet of the primary column to which the first intermediate stream connects.

8. The process according to claim 7 wherein the primary column comprises a condenser and the secondary column does not comprise a condenser.

9. The process according to claim 1 wherein the crude product stream further comprises an unreacted feed material comprising a dialkyl ester of a $C_5$ or $C_6$ di-carboxylic acid or an alkyl ester of a $C_5$ ketoacid, and the unreacted feed material is recovered in the reaction product stream.

10. The process according to claim 1, wherein the $C_5$ or $C_6$ alkanediol is a compound according to formula I:

Formula I

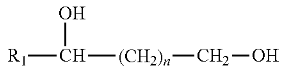

wherein either $R_1$ is H and n is 3 or 4; or $R_1$ is $CH_3$ and nis 2;

and wherein the $C_{10}$ or $C_{12}$ linear ester is a compound according to formula II:

Formula II

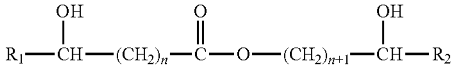

wherein either $R_1$ and $R_2$ are H and n is 3 or 4; or $R_1$ and $R_2$ are $CH_3$ and n is 2;

and wherein the $C_{10}$ or $C_{12}$ cyclic acetal or ketal is a compound according to Formula III:

Formula III

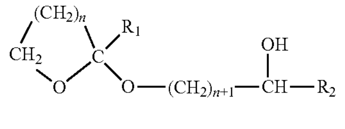

wherein either $R_1$ and $R_2$ are H and n is 3 or 4; or $R_1$ and $R_2$ are $CH_3$ and n is 2; and wherein the $C_5$ or $C_6$ cyclic ester is a compound according to formula IV:

Formula IV

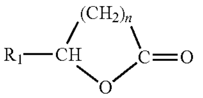

wherein either $R_1$ and $R_2$ are H and n is 3 or 4; or $R_1$ and $R_2$ are $CH_3$ and n is 2; and wherein the $C_5$ or $C_6$ aldehyde is a compound according to formula V:

Formula V

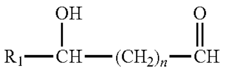

wherein either $R_1$ is H and n is 3 or 4; or $R_1$ is $CH_3$ and n is 2;

and the crude product stream optionally comprises a feed material or an unreacted feed material, and wherein, where present, the feed material or the unreacted feed material is a compound according to formula VI:

Formula VI

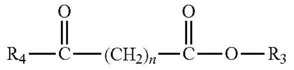

wherein $R_3$ is a $C_1$ to $C_5$ alkyl group, preferably a $C_1$ to $C_3$ alkyl group and most preferably methyl or ethyl, and wherein either: n is 2 and $R_4$ is $CH_3$; or n is 3 or 4, $R_4$ is $R_5$—O— and $R_5$ is a $C_1$ to $C_5$ alkyl group, preferably a $C_1$ to $C_3$ alkyl group and most preferably methyl or ethyl;

and wherein, the crude product stream optionally comprises an unreacted feed material comprising a dialkyl ester of a $C_5$ or $C_6$ di-carboxylic acid or an alkyl ester of a $C_5$ ketoacid, and where present, the $C_5$ or $C_6$ di-carboxylic acid or a $C_5$ ketoacid is a compound according to formula VII:

Formula VII

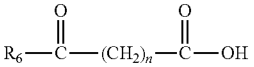

wherein either $R_6$ is OH and n is 3 or 4, or $R_6$ is $CH_3$ and n is 2.

11. The process according to claim 1, wherein the crude product stream optionally comprises a feed material or an unreacted feed material comprising a dialkyl ester of a $C_5$ or $C_6$ di-carboxylic acid or an alkyl ester of a $C_5$ ketoacid, and:

the $C_5$ or $C_6$ alkanediol is 1,6 hexanediol, the $C_{10}$ or $C_{12}$ linear ester is 6-hydroxyhexyl 6-hydroxyhexanoate, the $C_{10}$ or $C_{12}$ cyclic acetal or ketal is 6-(oxepan-2-yloxy) hexan-1-ol, the $C_5$ or $C_6$ cyclic ester is caprolactone, and the $C_5$ or $C_6$ aldehyde is 6-hydroxyhexanal, and wherein, where present, the feed material or the unreacted feed material is dialkyl adipate, and the $C_5$ or $C_6$ di-carboxylic acid or $C_5$ ketoacid is adipic acid;

or, the $C_5$ or $C_6$ alkanediol is 1,5 pentanediol and, where each is present, the $C_{10}$ or $C_{12}$ linear ester is 5-hydroxypentyl 5-hydroxypentanoate, the $C_{10}$ or $C_{12}$ cyclic acetal or ketal is 5-((tetrahydro-2H-pyran-2-yl)oxy) pentan-1-ol, the $C_5$ or $C_6$ cyclic ester is tetrahydro-2H-pyran-2-one, and the $C_5$ or $C_6$ aldehyde is 5-hydroxypentanal, and wherein, where present, the feed material or the unreacted feed material is dialkyl glutarate and the $C_5$ or $C_6$ di-carboxylic acid or $C_5$ ketoacid is glutaric acid, or, the $C_5$ or $C_6$ alkanediol is 1,4 pentanediol and, where each is present, the $C_{10}$ or $C_{12}$ linear ester is 4-hydroxypentyl 4-hydroxypentanoate, the $C_{10}$ or $C_{12}$ cyclic acetal or ketal is 5-((2-methyltetrahydrofuran-2-yl)oxy) pentan-2-ol, the $C_5$ or $C_6$ cyclic ester is gamma valerolactone, and the $C_5$ or $C_6$ aldehyde is 4-hydroxypentanal, and wherein, where present, the feed material or the unreacted feed material is alkyl levulinate, and the $C_5$ or $C_6$ di-carboxylic acid or $C_5$ ketoacid is levulinic acid.

12. The process according to claim 1, wherein the crude product stream optionally comprises a feed material or an unreacted feed material comprising a dialkyl ester of a $C_5$ or $C_6$ di-carboxylic acid or an alkyl ester of a $C_5$ ketoacid, wherein the $C_5$ or $C_6$ alkanediol is 1,6 hexanediol, the $C_{10}$ or $C_{12}$ linear ester is 6-hydroxyhexyl 6-hydroxyhexanoate, the $C_{10}$ or $C_{12}$ cyclic acetal or ketal is 6-(oxepan-2-yloxy) hexan-1-ol, the $C_5$ or $C_6$ cyclic ester is caprolactone, and the $C_5$ or $C_6$ aldehyde is 6-hydroxyhexanal, and wherein, where present, the feed material is dialkyl adipate, and the $C_5$ or $C_6$ di-carboxylic acid or $C_5$ ketoacid is adipic acid.

13. The process according to claim 1, wherein the crude product stream optionally comprises a feed material or an unreacted feed material comprising a dialkyl ester of a $C_5$ or $C_6$ di-carboxylic acid or an alkyl ester of a $C_5$ ketoacid, wherein the $C_5$ or $C_6$ alkanediol is 1,6 hexanediol, the $C_{10}$ or $C_{12}$ linear ester is 6-hydroxyhexyl 6-hydroxyhexanoate, the $C_{10}$ or $C_{12}$ cyclic acetal or ketal is 6-(oxepan-2-yloxy) hexan-1-ol, the $C_5$ or $C_6$ cyclic ester is caprolactone, and the $C_5$ or $C_6$ aldehyde is 6-hydroxyhexanal, and wherein, where present, the feed material or the unreacted feed material is dimethyl adipate, and the $C_5$ or $C_6$ di-carboxylic acid or $C_5$ ketoacid is adipic acid.

14. The process according to claim 1, wherein the crude product stream optionally comprises a feed material or an unreacted feed material comprising a dialkyl ester of a $C_5$ or $C_6$ di-carboxylic acid or an alkyl ester of a $C_5$ ketoacid, wherein the $C_5$ or $C_6$ alkanediol is 1,5 pentanediol and, where each is present, the $C_{10}$ or $C_{12}$ linear ester is 5-hydroxypentyl 5-hydroxypentanoate, the $C_{10}$ or $C_{12}$ cyclic acetal or ketal is 5-((tetrahydro-2H-pyran-2-yl)oxy) pentan-1-ol, the $C_5$ or $C_6$ cyclic ester is tetrahydro-2H-pyran-2-one, and the $C_5$ or $C_6$ aldehyde is 5-hydroxypentanal, and wherein, where present, the feed material or the unreacted feed material is dimethyl glutarate, and the $C_5$ or $C_6$ di-carboxylic acid or $C_5$ ketoacid is glutaric acid.

15. The process according to claim 1, wherein the crude product stream optionally comprises a feed material or an unreacted feed material comprising a dialkyl ester of a $C_5$ or $C_6$ di-carboxylic acid or an alkyl ester of a $C_5$ ketoacid, wherein the $C_5$ or $C_6$ alkanediol is 1,4 pentanediol and, where each is present, the $C_{10}$ or $C_{12}$ linear ester is 4-hydroxypentyl 4-hydroxypentanoate, the $C_{10}$ or $C_{12}$ cyclic acetal or ketal is 5-((2-methyltetrahydrofuran-2-yl)oxy) pentan-2-ol, the $C_5$ or $C_6$ cyclic ester is gamma valerolactone, and the $C_5$ or $C_6$ aldehyde is 4-hydroxypentanal, and wherein, where present, the feed material or the unreacted feed material is methyl levulinate, and the $C_5$ or $C_6$ di-carboxylic acid or $C_5$ ketoacid is levulinic acid.

16. A process for separating a $C_5$ or $C_6$ alkanediol from a crude product stream comprising the $C_5$ or $C_6$ alkanediol and heavy contaminants comprising one or more of a $C_{10}$ or $C_{12}$ linear ester, or a $C_{10}$ or $C_{12}$ cyclic acetal or ketal, the process comprising:

feeding the crude product stream to a separation system comprising a first distillation zone, to which the crude product stream is fed and from which the heavy contaminants are removed in a heavies stream taken as a bottom stream, and a second distillation zone, in which the $C_5$ or $C_6$ alkanediol is separated from a reaction product, comprising one or more of a $C_5$ or $C_6$ cyclic ester, or a $C_5$ or $C_6$ aldehyde, formed in the first distillation zone and from which the $C_5$ or $C_6$ alkanediol is withdrawn in a refined product stream, wherein the first and second distillation zones are contained within a single column, the second distillation zone being separated from the first distillation zone by a baffle that starts at the bottom of the column and extends above both a feed point where the crude product stream is fed to the first distillation zone and a withdrawal point where the refined product stream is withdrawn from the second distillation zone.

17. The process according to claim 16, wherein the $C_5$ or $C_6$ alkanediol is 1,6 hexanediol.

* * * * *